United States Patent
Rong et al.

(10) Patent No.: US 11,773,103 B2
(45) Date of Patent: Oct. 3, 2023

(54) IRAK4 DEGRADERS AND USES THEREOF

(71) Applicant: Kymera Therapeutics, Inc., Watertown, MA (US)

(72) Inventors: Haojing Rong, Watertown, MA (US); Brad Enerson, Watertown, MA (US)

(73) Assignee: Kymera Therapeutics, Inc., Watertown, MA (US)

( * ) Notice: Subject to any disclaimer, the term of this patent is extended or adjusted under 35 U.S.C. 154(b) by 0 days.

(21) Appl. No.: 17/651,202

(22) Filed: Feb. 15, 2022

(65) Prior Publication Data

US 2022/0274993 A1    Sep. 1, 2022

Related U.S. Application Data

(60) Provisional application No. 63/149,625, filed on Feb. 15, 2021.

(51) Int. Cl.
*C07D 487/04*    (2006.01)
*A61P 29/00*    (2006.01)

(52) U.S. Cl.
CPC ............ *C07D 487/04* (2013.01); *A61P 29/00* (2018.01)

(58) Field of Classification Search
CPC .............................. C07D 487/04; A61P 29/00
See application file for complete search history.

(56) References Cited

U.S. PATENT DOCUMENTS

| | | |
|---|---|---|
| 7,390,799 B2 | 6/2008 | Bruncko et al. |
| 7,501,496 B1 | 3/2009 | Endl et al. |
| 8,138,347 B2 | 3/2012 | Knight et al. |
| 8,906,682 B2 | 12/2014 | June et al. |
| 11,117,889 B1 | 9/2021 | Mainolfi et al. |
| 11,352,350 B2 | 6/2022 | Mainolfi et al. |
| 2001/0053782 A1 | 12/2001 | Blumenkopf et al. |
| 2004/0029902 A1 | 2/2004 | Singh et al. |
| 2004/0106569 A1 | 6/2004 | Klippel-Giese et al. |
| 2004/0116421 A1 | 6/2004 | Kawashima et al. |
| 2004/0242631 A1 | 12/2004 | Garlich et al. |
| 2005/0014802 A1 | 1/2005 | Attardo et al. |
| 2005/0075306 A1 | 4/2005 | Schreiber et al. |
| 2006/0211657 A1 | 9/2006 | Singh et al. |
| 2007/0098719 A1 | 5/2007 | Smith et al. |
| 2007/0135461 A1 | 6/2007 | Rodgers et al. |
| 2007/0191405 A1 | 8/2007 | Noronha et al. |
| 2008/0076768 A1 | 3/2008 | Chuckowree et al. |
| 2008/0108636 A1 | 5/2008 | Honigberg et al. |
| 2008/0194579 A1 | 8/2008 | Garcia-Echeverria et al. |
| 2008/0275067 A1 | 11/2008 | Fowler et al. |
| 2009/0055944 A1 | 2/2009 | Korman et al. |
| 2009/0136494 A1 | 5/2009 | Ponath et al. |
| 2009/0233903 A1 | 9/2009 | Rodgers et al. |
| 2010/0087440 A1 | 4/2010 | Bajjalieh et al. |
| 2010/0150892 A1 | 6/2010 | Han |
| 2010/0197671 A1 | 8/2010 | Burns et al. |
| 2010/0197686 A1 | 8/2010 | Xing et al. |
| 2010/0203056 A1 | 8/2010 | Irving et al. |
| 2010/0233183 A1 | 9/2010 | Triebel et al. |
| 2010/0249092 A1 | 9/2010 | Singh et al. |
| 2010/0249126 A1 | 9/2010 | Burger et al. |
| 2011/0008331 A1 | 1/2011 | Triebel |
| 2011/0053941 A1 | 3/2011 | Mautino et al. |
| 2011/0136796 A1 | 6/2011 | Mautino et al. |
| 2011/0165156 A1 | 7/2011 | Dimoudis et al. |
| 2011/0274683 A1 | 11/2011 | Wong et al. |
| 2012/0189639 A1 | 7/2012 | Schebye et al. |
| 2012/0277217 A1 | 11/2012 | Mautino et al. |
| 2012/0329997 A1 | 12/2012 | Fertig et al. |
| 2013/0005949 A1 | 1/2013 | Fertig et al. |
| 2013/0149236 A1 | 6/2013 | Johnson et al. |
| 2014/0066625 A1 | 3/2014 | Mautino et al. |
| 2014/0079699 A1 | 3/2014 | Wong et al. |
| 2014/0079706 A1 | 3/2014 | Cannarile et al. |
| 2014/0093511 A1 | 4/2014 | Lonberg et al. |
| 2014/0336363 A1 | 11/2014 | Fertig et al. |
| 2014/0341917 A1 | 11/2014 | Nastri et al. |
| 2017/0065719 A1 | 3/2017 | Qian et al. |
| 2019/0192668 A1 | 6/2019 | Mainolfi et al. |
| 2019/0374528 A1 | 12/2019 | Gray et al. |
| 2021/0395273 A1 | 12/2021 | Zheng et al. |

FOREIGN PATENT DOCUMENTS

| | | |
|---|---|---|
| WO | WO-2001042246 A2 | 6/2001 |
| WO | WO-2002088112 A1 | 11/2002 |
| WO | WO-2003063794 A2 | 8/2003 |
| WO | WO-2004019973 A1 | 3/2004 |
| WO | WO-2004089925 A1 | 10/2004 |
| WO | WO-2004106328 A1 | 12/2004 |
| WO | WO-2005007623 A2 | 1/2005 |
| WO | WO-2005113554 A2 | 12/2005 |
| WO | WO-2006029879 A2 | 3/2006 |
| WO | WO-2006078846 A1 | 7/2006 |

(Continued)

OTHER PUBLICATIONS

Adams et al., "Big opportunities for small molecules in immuno-oncology," Nat Rev Drug Discov. 2015;14(9):603-22.
Berge et al., "Pharmaceutical salts," J Pharm Sci. 1977;66(1):1-19.
Berndsen et al., "New insights into ubiquitin E3 ligase mechanism," Nat Struct Mol Biol. 2014;21(4):301-7.
Blake et al., "Studies with deuterated drugs," J Pharm Sci. 1975;64(3):367-91.
Buckley et al., "IRAK-4 inhibitors. Part 1: a series of amides," Bioorg Med Chem Lett. 2008;18(11):3211-4.
Buckley et al., "IRAK-4 inhibitors. Part II: a structure-based assessment of imidazo[1,2-a]pyridine binding," Bioorg Med Chem Lett. 2008;18(11):3291-5.

(Continued)

*Primary Examiner* — Erich A Leeser

(74) *Attorney, Agent, or Firm* — Dechert LLP; Andrea L. C. Reid; Todd K. Macklin

(57) ABSTRACT

The present invention relates to a method of treating autoimmune/autoinflammatory diseases and hematological malignancies in a subject.

25 Claims, No Drawings

(56) References Cited

FOREIGN PATENT DOCUMENTS

| WO | WO-2006105021 A2 | 10/2006 | |
| WO | WO-2006122806 A2 | 11/2006 | |
| WO | WO-2007005874 A2 | 1/2007 | |
| WO | WO-2007044729 A2 | 4/2007 | |
| WO | WO-2007053452 A1 | 5/2007 | |
| WO | WO-2007070514 A1 | 6/2007 | |
| WO | WO-2007084786 A1 | 7/2007 | |
| WO | WO-2007129161 A2 | 11/2007 | |
| WO | WO-2008039218 A2 | 4/2008 | |
| WO | WO-2008109943 A1 | 9/2008 | |
| WO | WO-2008118802 A1 | 10/2008 | |
| WO | WO-2008132601 A1 | 11/2008 | |
| WO | WO-2009009116 A2 | 1/2009 | |
| WO | WO-2009044273 A2 | 4/2009 | |
| WO | WO-2009073620 A2 | 6/2009 | |
| WO | WO-2009114512 A1 | 9/2009 | |
| WO | WO-2009132238 A3 | 10/2009 | |
| WO | WO-2010019570 A2 | 2/2010 | |
| WO | WO-2010077634 A1 | 7/2010 | |
| WO | WO-2011028683 A1 | 3/2011 | |
| WO | WO-2011056652 A1 | 5/2011 | |
| WO | WO-2011070024 A1 | 6/2011 | |
| WO | WO-2011090760 A1 | 7/2011 | |
| WO | WO-2011107553 A1 | 9/2011 | |
| WO | WO-2011109400 A2 | 9/2011 | |
| WO | WO-2011131407 A1 | 10/2011 | |
| WO | WO-2011140249 A2 | 11/2011 | |
| WO | WO-2012032433 A1 | 3/2012 | |
| WO | WO-2012145493 A1 | 10/2012 | |
| WO | WO-2013079174 A1 | 6/2013 | |
| WO | WO-2013087699 A1 | 6/2013 | |
| WO | WO-2013119716 A1 | 8/2013 | |
| WO | WO-2013132044 A1 | 9/2013 | |
| WO | WO-2013169264 A1 | 11/2013 | |
| WO | WO-2014008218 A1 | 1/2014 | |
| WO | WO-2014036357 A1 | 3/2014 | |
| WO | WO-2014142237 A1 | 9/2014 | |
| WO | WO-2016144846 A1 | 9/2016 | |
| WO | WO-2016169989 A1 | 10/2016 | |
| WO | WO-2018089736 A1 | 5/2018 | |
| WO | WO-2019133531 A1 | 7/2019 | |
| WO | WO-2020010227 A1 | 1/2020 | |
| WO | WO 2020/113233 | * 6/2020 | ........... A61K 39/395 |
| WO | WO-2020113233 A1 | 6/2020 | |
| WO | WO-2021247899 A1 | 12/2021 | |

OTHER PUBLICATIONS

Buckley et al., "IRAK-4 inhibitors. Part III: A series of imidazo[1,2-a]pyridines," Bioorg Med Chem Lett. 2008;18(12):3656-60.

Cameron et al., "Loss of Interleukin Receptor-Associated Kinase 4 Signaling Suppresses Amyloid Pathology and Alters Microglial Phenotype in a Mouse Model of Alzheimer's Disease," J Neurosci. 2012;32(43):15112-23.

Cario, "Therapeutic Impact of Toll-like Receptors on Inflammatory Bowel Diseases: A Multiple-edged Sword," Inflamm Bowel Dis. 2008;14(3):411-21.

Chou and Talalay, "Quantitative analysis of dose-effect relationships: the combined effects of multiple drugs or enzyme inhibitors," Adv Enzyme Regul. 1984;22:27-55.

Cohen et al., "Targeting protein kinases for the development of anti-inflammatory drugs," Curr Opin Cell Biol. 2009;21(2):17-24.

Crews, "Targeting the Undruggable Proteome: The Small Molecules of My Dreams," Chem Biol. 2010;17(6):551-5.

Cushing et al., "Interleukin 1/Toll-like receptor-induced autophosphorylation activates interleukin 1 receptor-associated kinase 4 and controls cytokine induction in a cell type-specific manner," J Biol Chem. 2014;289(15):10865-10875.

Dalbeth et al., "Hyperuricaemia and gout: state of the art and future perspectives," Ann Rheum Dis. 2014;73(9):1598-600.

De Nardo et al. "Interleukin-1 receptor-associated kinase 4 (IRAK4) plays a dual role in myddosome formation and Toll-like receptor signaling," J Biol Chem. 2018;293(39):15195-15207.

Deshaies and Joazeiro, "RING domain E3 ubiquitin ligases," Annu Rev Biochem. 2009;78:399-434.

Dinarello, "IL-1: Discoveries, controversies and future directions," Eur J Immunol. 2010:40(3):599-606.

Dinarello, "Interleukin 1 and interleukin 18 as mediators of inflammation and the aging process," Am J Clin Nutr. 2006;83(suppl):447S-55S.

Dinarello, "Interleukin-18 and the Pathogenesis of Inflammatory Diseases," Semin Nephrol. 2007;27(1):98-114.

Fisher et al., "The complexities inherent in attempts to decrease drug clearance by blocking sites of CYP-mediated metabolism," Curr Opin Drug Discov Devel. 2006;9(1):101-9.

Flannery et al., "The interleukin-1 receptor-associated kinases: Critical regulators of innate immune signaling," Biochem Pharmacol. 2010;80(12):1981-91.

Foster, "Deuterium isotope effects in the metabolism of drugs and xenobiotics: implications for drug design," Advances in Drug Research. 1985;14:1-40.

Fukuto et al., "Determination of the mechanism of demethylation of (methylenedioxy)phenyl compounds by cytochrome P450 using deuterium isotope effects," J Med Chem. 1991;34(9):2871-6.

Gearing, "Targeting toll-like receptors fordrug development: a summary of commercial approaches," Immunol Cell Biol. 2007;85(6):490-4.

Geyer and Müller-Ladner, "Actual status of antiinterleukin-1 therapies in rheumatic diseases," Curr Opin Rheumatol. 2010;22(3):246-51.

Gottipati et al., "IRAK1: A critical signaling mediator of innate immunity," Cell Signal. 2008;20(2):269-76.

Hennessy et al., "Targeting Toll-like receptors: emerging therapeutics?" Nat Rev Drug Discov. 2010;9(4):293-307.

Hoffman et al., "Efficacy and Safety of Rilonacept (Interleukin-1 Trap) in Patients with Cryopyrin-Associated Periodic Syndromes," Arthritis Rheum. 2008;58(8):2443-5.

Iannello et al., "Role of Interleukin-18 in the Development and Pathogenesis of AIDS," AIDS Rev. 2009;11(3):115-25.

Iriyama et al., "Clinical significance of genetic mutations of CD79B, CARD11, MYD88, and EZH2 genes in diffuse large B-cell lymphoma patients" 53rd ASH Annual Meeting, San Diego, California, Dec. 10-13, 2011.

Kim et al., "A critical role for IRAK4 kinase activity in Toll-like receptor-mediated innate immunity," J Exp Med. 2007;204(5):1025-36.

Koziczak-Holbro et al., "IRAK-4 Kinase Activity Is Required for Interleukin-1 (IL-1) Receptor- and Toll-like Receptor 7-mediated Signaling and Gene Expression," J Biol Chem. 2007;282(18):13552-60.

Ku et al., "Selective predisposition to bacterial infections in IRAK-4-deficient children: IRAK-4-dependent TLRs are otherwise redundant in protective immunity," J Exp Med. 2007;204(10):2407-2422.

Kubo-Murai et al., "IRAK4-dependent Degradation of IRAK-1 is a Negative Feedback Signal for TLR-mediated NF-kB Activation," J Biochem. 2008;143(3):295-302.

Kushner et al., "Pharmacological uses and perspectives of heavy water and deuterated compounds," Can J Physiol Pharmacol. 1999;77(2):79-88.

Lebakken et al., "A Fluorescence Lifetime Based Binding Assay to Characterize Kinase Inhibitors," J Biomol Screen. 2007;12(6):828-41.

Li et al., "Genome-wide and functional annotation of human E3 ubiquitin ligases identifies MULAN, a mitochondrial E3 that regulates the organelle's dynamics and signaling," PLoS One. 2008;3(1):e1487.

Li et al., "IRAK-4: A novel member of the IRAK family with the properties of an IRAK-kinase," Proc Natl Acad Sci USA. 2002;99(8):5567-72.

Li, "IRAK4 in TLR/IL-1R signaling: Possible clinical applications," Eur J Immunol. 2008;38(3):614-8.

Lin et al., "Helical assembly in the MyD88-IRAK4-IRAK2 complex in TLR/IL-1R signalling," Nature. 2010:465(7300):885-90.

Lust et al., "Induction of a Chronic Disease State in patients With Smoldering of Indolent Multiple Myeloma by Targeting Interleukin

(56) References Cited

OTHER PUBLICATIONS

Iß-Induced Interleukin 6 Production and the Myeloma Proliferative Component," Mayo Clin Proc. 2009;84(2):114-22.
Martinon et al., "Gout-associated uric acid crystals activate the NALP3 inflammasome," Nature. 2006;440(7081):237-41.
Maschera et al., "Overexpression of an enzymatically inactive interleukin-1-receptor-associated kinase activates nuclear factor-kB," Biochem J. 1999;339(Pt2):227-31.
Ngo et al., "Oncogenically active MYD88 mutations in human lymphoma," Nature. 2011;470(7332):115-9.
Okazaki et al., "A rheostat for immune responses: the unique properties of PD-1 and their advantages for clinical application," Nat. Immunol. 2013; 14(12): 1212-1218.
Patra and Choi, "Recent Progress in the Molecular Recognition and Therapeutic Importance of Interleukin-1 Receptor-Associated Kinase 4," Molecules. 2016;21(11):1529.
PCT International Search Report from PCT/US2021/035745 dated Sep. 27, 2021.
PCT International Search Report from PCT/US2021/035747 dated Sep. 27, 2021.
PCT International Search Report from PCT/US2022/070662 dated Apr. 18, 2022.
PCT International Search Report from PCT/US2022/070664 dated May 3, 2022.
Picard et al., "Clinical features and outcome of patients with IRAK-4 and MyD88 deficiency," Medicine (Baltimore). 2010;89(6):403-425.
Picard et al., "Inherited human IRAK-4 deficiency: an update," Immunol Res. 2007;38(1-3):347-52.
Powers et al., "Discovery and initial SAR of inhibitors of interleukin-1 receptor-associated kinase-4," Bioorg Med Chem Lett. 2006;16(11):2842-5.
Ramirez et al., "Defining causative factors contributing in the activation of hedgehog signaling in diffuse large B-cell lymphoma," Leuk. Res. 2012;36(10): 1267-73.
Rokosz et al., "Kinase inhibitors as drugs for chronic inflammatory and immunological diseases: progress and challenges," Expert Opin Ther Targets. 2008;12(7):883-903.
Ross et al., "Bispecific T cell engager (BITE®) antibody constructs can mediate bystander tumor cell killing," PLoS ONE. 2017; 12(8): eQ183390.
Schneekloth and Crews, "Chemical Approaches to Controlling Intracellular Protein Degradation," Chembiochem. 2005;6(1): 40-46.
Sen et al., "Transcriptional signaling by double-stranded RNA: role of TLR3," Cytokine Growth Factor Rev. 2005;16(1):1-14.
So et al., "A pilot study of IL-1 inhibition by anakinra in acute gout," Arthritis Res Ther. 2007;9(2):R28.
Song et al., "The kinase activities of interleukin-e receptor associated kinase (IRAK)-1 and 4 are redundant in the control of inflammatory cytokine expression in human cells," Mol Immunol. 2009;46(7):1458-66.
Spratt et al., "RBR E3 ubiquitin ligases: new structures, new insights, new question," Biochem J. 2014;458(3);421-37.
Suzuki et al., "IRAK-4 as the central TIR signaling mediator in innate immunity," Trends Immunol. 2002;23(10):503-6.
Suzuki et al., "Severe impairment of interleukin-1 and Toll-like receptor signalling in mice lacking IRAK-4," Nature. 2002;416(6882):750-6.
Swantek et al., "IL-1 Receptor-Associated Kinase Modulates Host Responsiveness to Endotoxin," Journal of Immunology 164: 4301-4306, J Immunol. 2000;164(8):4301-6.
Terkeltaub et al., "The interleukin 1 inhibitor rilonacept in treatment of chronic gouty arthritis: results of a placebo-controlled, monosequence crossover, non-randomised, single-blind pilot study," Ann Rheum Dis. 2009;68(10):1613-7.
Terkeltaub, "Update on gout: new therapeutic strategies and options," Nat Rev Rheumatol. 2010;6(1):30-8.
Toogood, "Small molecule immuno-oncology therapeutic agents," Bioorg. Med. Chem. Lett. 2018;28(3):319-329.
Torres et al., "Hyperalgesia, synovitis and multiple biomarkers of inflammation are suppressed by interleukin 1 inhibition in a novel animal model of gouty arthritis," Ann Rheum Dis. 2009;68(10):1602-8.
Treon et al., "Whole genome sequencing reveals a widely expressed mutation (MYD88 L265P) with oncogenic activity in Waldenström's Macroglobulinemia" 53rd ASH Annual Meeting, San Diego, California, Dec. 10-13, 2011 [abstract].
Trøseid et al., "The role of interleukin-18 in the metabolic syndrome," Cardiovasc Diabetol. 2010;9:11.
Wang et al., "IRAK-4 Inhibitors for Inflammation," Curr Top Med Chem. 2009;9(8):724-37.
Wang et al., "Roles of F-box proteins in cancer," Nat Rev Cancer. 2014;14(4):233-47.
Weaver, "Epidemiology of gout," Cleve Clin J Med. 2008;75 Suppl 5:S9-12.
Xu et al., "A somatic variant in MYD88 (L256P) revealed by whole genome sequencing differentiates lymphoplasmacytic lymphoma from marginal zone lymphomas" 53rd ASH Annual Meeting, San Diego, California, Dec. 10-13, 2011.
Yang et al., "Disruption of MYD88 pathway signaling leads to loss of constitutive IRAKI, NK-kB and JAK/STAT signaling and induces apoptosis of cells expressing the MYD88 L265P mutation in Waldenström's Macroglobulinemia" 53rd ASH Annual Meeting, San Diego, California, Dec. 10-13, 2011.
Zou et al., "PD-L1 (B7-H1) and PD-1 pathway blockage for cancer therapy: Mechanisms, response biomarkers, and combinations," Sci Transl. Med. 2016;8(328):328rv4.

* cited by examiner

IRAK4 DEGRADERS AND USES THEREOF

This application claims the benefit of U.S. Provisional Appl. No. 63/149,625, filed February 15, the entirety of which is herein incorporated by reference.

TECHNICAL FIELD OF THE INVENTION

The present invention relates to methods of administering IRAK4 degrader 5-((1R,4R)-2-oxa-5-azabicyclo[2.2.1]heptan-5-yl)-N-(3-(difluoromethyl)-1-((1r,4R)-4-((4-((3-(1-(2,6-dioxopiperidin-3-yl)-3-methyl-2-oxo-2,3-dihydro-1H-benzo[d]imidazol-4-yl)prop-2-yn-1-yl)oxy)piperidin-1-yl)methyl)cyclohexyl)-1H-pyrazol-4-yl)pyrazolo[1,5-a]pyrimidine-3-carboxamide (Compound A), and uses thereof for treating autoinflammatory/autoimmune diseases and hematological malignancies.

BACKGROUND OF THE INVENTION

Ubiquitin-Proteasome Pathway (UPP) is a critical pathway that regulates key regulator proteins and degrades misfolded or abnormal proteins. UPP is central to multiple cellular processes, and if defective or imbalanced, it leads to pathogenesis of a variety of diseases. The covalent attachment of ubiquitin to specific protein substrates is achieved through the action of E3 ubiquitin ligases.

UPP plays a key role in the degradation of short-lived and regulatory proteins important in a variety of basic cellular processes, including regulation of the cell cycle, modulation of cell surface receptors and ion channels, and antigen presentation. Interleukin-1 receptor-associated kinase-4 (IRAK4) is a key component of the myddosome, a multiprotein complex involved in innate immunity that mediates signaling through toll-like receptors (TLRs) and interleukin (IL)-1 receptors (Patra and Choi, Molecule 2016, 21(11): 1529). The IRAK4 protein is ubiquitously expressed across multiple different tissue types, including skin, lymphoid tissue, bone marrow, gastrointestinal (GI) tract and lung. The function of IRAK4 is dependent both on its kinase activity and on its scaffolding properties, which is required for the assembly of the myddosome complex following TLR or IL-1R engagement and myeloid differentiation factor 88 (MyD88) activation (De Nardo et al., J. Bio. Chem. 2018, 293(39):15195; Cushing et al., J. Bio. Chem. 2014, 289(15): 10865). The NF-kB activation is particularly dependent on the scaffolding function of IRAK4 and is a key driver of cellular proliferation and proinflammatory cytokine and chemokine production mediated by myddosome activation.

There are numerous cutaneous, rheumatic, and GI autoinflammatory/autoimmune disease indications whose pathogenesis involves IL-1 family cytokines as well as TLR stimulation and where the pleiotropic effects of an IRAK4 degrader on these pathways can provide a significant advantage over current treatment options. Further there are multiple cutaneous indications where there is clinical proof of concept for targeting the IL-1R/TLR pathway but continued high unmet need for more effective therapeutics.

SUMMARY OF THE INVENTION

It has been found that the administration of IRAK4 degrader 5-((1R,4R)-2-oxa-5-azabicyclo[2.2.1]heptan-5-yl)-N-(3-(difluoromethyl)-1-((1r,4R)-4-((4-((3-(1-(2,6-dioxopiperidin-3-yl)-3-methyl-2-oxo-2,3-dihydro-1H-benzo[d]imidazol-4-yl)prop-2-yn-1-yl)oxy)piperidin-1-yl)methyl)cyclohexyl)-1H-pyrazol-4-yl)pyrazolo[1,5-a]pyrimidine-3-carboxamide (Compound A) achieving certain pharmacokinetic parameters of the disclosure has certain advantages in treating autoimmune/autoinflammatory diseases and hematological malignancies. For example, it has been found that the no observed adverse effect level (NOAEL) in dogs, the most sensitive species, is 60 mg/kg/day, which corresponded to average, sex-combined, maximum observed concentration ($C_{max}$) in plasma and area under the concentration-time curve ($AUC_{0-24}$) values of 561 ng/mL and 11,700 ng*hr/mL, respectively for Compound A; 288 ng/mL and 6090 ng*hr/mL, respectively, for Compound B; and 265 ng/mL and 5620 ng*hr/mL, respectively, for Compound C on Day 42 of the dosing phase.

Accordingly, in one embodiment of the present methods and uses, there is provided a method of treating an autoimmune/autoinflammatory disease and/or a hematological malignancy, comprising administering to a patient in need thereof a therapeutically effective amount of Compound A, or a pharmaceutically acceptable salt thereof, and/or composition thereof, wherein a $C_{max}$ of Compound A in plasma is up to about 561 ng/mL.

In one embodiment of the present methods and uses, there is provided a method of treating an autoimmune/autoinflammatory disease and/or a hematological malignancy, comprising administering to a patient in need thereof a therapeutically effective amount of Compound A, or a pharmaceutically acceptable salt thereof, and/or composition thereof, wherein a $C_{max}$ of Compound B in plasma is up to about 288 ng/mL.

In one embodiment of the present methods and uses, there is provided a method of treating an autoimmune/autoinflammatory disease and/or a hematological malignancy, comprising administering to a patient in need thereof a therapeutically effective amount of Compound A, or a pharmaceutically acceptable salt thereof, and/or composition thereof, wherein a $C_{max}$ of Compound C in plasma is up to about 265 ng/mL.

In one embodiment of the present methods and uses, there is provided a method of treating an autoimmune/autoinflammatory disease and/or a hematological malignancy, comprising administering to a patient in need thereof a therapeutically effective amount of Compound A, or a pharmaceutically acceptable salt thereof, and/or composition thereof, wherein an $AUC_{0-24}$ of Compound A in plasma is up to about 11700 ng*hr/mL.

In one embodiment of the present methods and uses, there is provided a method of treating an autoimmune/autoinflammatory disease and/or a hematological malignancy, comprising administering to a patient in need thereof a therapeutically effective amount of Compound A, or a pharmaceutically acceptable salt thereof, and/or composition thereof, wherein an $AUC_{0-24}$ of Compound B in plasma is up to about 6090 ng*hr/mL.

In one embodiment of the present methods and uses, there is provided a method of treating an autoimmune/autoinflammatory disease and/or a hematological malignancy, comprising administering to a patient in need thereof a therapeutically effective amount of Compound A, or a pharmaceutically acceptable salt thereof, and/or composition thereof, wherein an $AUC_{0-24}$ of Compound C in plasma is up to about 5620 ng*hr/mL.

In one embodiment of achieving the $AUC_{0-24}$ of Compound A, Compound B, or Compound C, Compound A is administered at a dose of about 10 mg/kg to about 200 mg/kg, for example, Compound A is administered at a dose selected from about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, and about 90 mg/kg.

In some embodiments, the $T_{max}$ of Compound A is achieved in about 4 hrs to about 12 hrs, for example, about 4, about 5, about 6, about 7, about 8, about 9, about 10, about 11, or about 12 hrs.

In some aspects, the autoimmune/autoinflammatory disease is selected from a cutaneous, rheumatic, and gastrointestinal autoimmune/autoinflammatory disease. In some aspects, the autoimmune/autoinflammatory disease is a cutaneous autoimmune/autoinflammatory disease selected from atopic dermatitis (AD) and hidradenitis suppurativa (HS).

These and other aspects of this disclosure will be apparent upon reference to the following detailed description. To this end, various references are set forth herein which describe in more detail certain background information and procedures and are each hereby incorporated by reference in their entirety.

DETAILED DESCRIPTION OF THE INVENTION

1. General Description of Certain Embodiments of the Invention

Compound A is a potent, highly selective, orally administered heterobifunctional small molecule therapeutic targeting IRAK4 and the E3 ligase CRBN to mediate the selective degradation of IRAK4 via the ubiquitin-proteasome system.

Compound A is composed of a CRBN-targeting ligand and an IRAK4-targeting ligand joined by a chemical linker. Compound A forms a ternary complex through non-covalent binding to both CRBN and IRAK4, bringing the E3 ligase (CRBN) in close proximity to IRAK4, that now serves as its neosubstrate. This proximity leads to IRAK4 ubiquitination and proteosomal degradation and eventual release of Compound A, which is then free to mediate additional rounds of ternary complex formation and IRAK4 degradation.

In vitro and in vivo studies confirmed the ability of Compound A to selectively degrade its intended target, IRAK4, and to inhibit downstream production of disease relevant proinflammatory cytokines and chemokines. In vitro, Compound A's ability to degrade IRAK4 across species was confirmed in a study of mouse and rat splenocytes and dog, monkey, and human PBMCs, where similar $DC_{50}$ values were observed across all species (<10 nM). Across a series of in vitro studies in human peripheral blood mononuclear cells (PBMCs), whole blood, and OCI-LY10 cells, Compound A robustly reduced IRAK4 levels, with $DC_{50}$ values consistently in the low nM range. Multiple in vitro cytokine release assays confirmed Compound A's ability to inhibit TLR agonist (lipopolysaccharide and R848) and IL-1β-induced proinflammatory cytokine production (including IL-6, TNF-α, granulocyte-macrophage colony-stimulating factor, and IL-8) in PBMCs with IC50 values also in the low nM range. Lastly, mass spectrometry (MS) proteomic analysis of PBMCs treated with Compound A demonstrated the compound's selectivity for its target, with IRAK4 being the only protein degraded of more than 9,000 proteins sampled.

In vivo, murine models of inflammation demonstrated the ability of Compound A-induced IRAK4 degradation to impact TLR- and IL-1β-mediated Th1 and Th17 inflammation as well as neutrophil migration. In the mouse air pouch model of MSU-crystal induced (TLR 2/4-dependent) inflammation, 3 days twice daily administration of Compound A at doses ranging from 30 to 100 mg/kg not only significantly reduced IRAK4 levels in the spleen, but also significantly reduced the inflammatory exudate, including reduction of neutrophils and IL-1β. Similar findings were observed in the imiquimod psoriasis model (TLR 7/8-dependent), where administration of Compound A resulted in dose-dependent degradation of IRAK4 in the spleen and skin associated with reduction in skin thickness as well as significant reduction of IL-1β ($p<0.0001$) and IL-6 ($p<0.05$; 300 mg/kg only) in the skin. Overall, efficacy was associated with achieving at least 80% or more IRAK4 knockdown in associated tissues in the model systems.

In vivo pharmacokinetics (PK)/pharmacodynamics (PD) studies in mice and dogs demonstrated potent IRAK4 degradation by Compound A. In wild-type mice, a single oral dose of Compound A at 300 mg/kg resulted in nearly 100% degradation of IRAK4 in the skin and approximately 66% degradation in the spleen, which was sustained for at least 48-hour post-dose. In both the skin and spleen, maximal PD effects were achieved after tmax at each dose level. In dogs, 7 days of oral administration at doses up to 10 mg/kg/day also led to marked reduction of IRAK4 in the skin and in PBMCs, with Compound A trough plasma concentration levels as low as 3 nM inducing >85% degradation of IRAK4 in the PBMCs and degradation below the limit of quantitation in the skin. Recovery of IRAK4 levels was noted by 96 to 168 hr following last dose in dogs, demonstrating the reversible nature of Compound A induced degradation. Together, these studies point to the potent, on-target, and reversible effects of Compound A against IRAK4.

In in vivo pharmacokinetic (PK) studies conducted in rats, dogs, and monkeys, Compound A PK was characterized by moderate to high clearance, high volume of distribution at steady state, a moderate terminal half-life, and low to moderate bioavailability. Compound A exhibited low solubility, moderate permeability, and was identified as a substrate of P-glycoprotein (P-gp) and breast cancer resistance protein (BCRP) in vitro. Compound A was highly bound to plasma proteins across nonclinical species and humans and did not significantly partition into red blood cells. In distribution studies in rats, Compound A extensively distributed into tissues, but had limited penetration into the central nervous system (CNS).

In vitro and in vivo metabolism studies showed that Compound A underwent oxidative metabolism via cytochrome P450 (CYP). An excretion study conducted in bile duct-cannulated (BDC) rats showed negligible renal clearance of Compound A, and minor to moderate biliary and intestinal excretion as parent drug. Metabolites generated in liver microsomes from humans were also detected in those from rat, dog, and monkey. In the in vitro drug-drug interaction studies, Compound A demonstrated potential time dependent inhibition (TDI) of CYP2C19 and CYP3A4 and inhibited BCRP efflux, and therefore has the potential to be a perpetrator to sensitive CYP2C19, CYP3A4, and BCRP substrates. Conversely, Compound A is primarily metabolized by CYP3A4 and is substrate of P-gp and BCRP and has the potential to be a victim when co-dosing with strong or moderate inhibitors or inducers of the enzymes.

Accordingly, in some embodiments, the present disclosure provides a method of treating an autoimmune/autoinflammatory disease and/or a hematological malignancy, comprising administering to a patient in need thereof a therapeutically effective amount of Compound A, or a pharmaceutically acceptable salt thereof, and/or composition thereof, wherein a $C_{max}$ of Compound A in plasma is up to about 561 ng/mL.

In some embodiments, the present disclosure provides a method of treating an autoimmune/autoinflammatory disease and/or a hematological malignancy, comprising administering to a patient in need thereof a therapeutically effective amount of Compound A, or a pharmaceutically acceptable salt thereof, and/or composition thereof, wherein an $AUC_{0-24}$ of Compound A in plasma is up to about 11700 ng*hr/mL.

In some embodiments, an autoimmune/autoinflammatory disease is selected from atopic dermatitis (AD) and hidradenitis suppurativa (HS).

In the following disclosure, certain specific details are set forth in order to provide a thorough understanding of various embodiments. However, one skilled in the art will understand that the methods and uses described herein may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

2. Definitions

As used in the specification and appended claims, unless specified to the contrary, the following terms and abbreviations have the meaning indicated:

"Compound A" refers to IRAK4 degrader 5-((1R,4R)-2-oxa-5-azabicyclo[2.2.1]heptan-5-yl)-N-(3-(difluoromethyl)-1-((1r,4R)-4-((4-((3-(1-(2,6-dioxopiperidin-3-yl)-3-methyl-2-oxo-2,3-dihydro-1H-benzo[d]imidazol-4-yl)prop-2-yn-1-yl)oxy)piperidin-1-yl)methyl)cyclohexyl)-1H-pyrazol-4-yl)pyrazolo[1,5-a]pyrimidine-3-carboxamide, of formula:

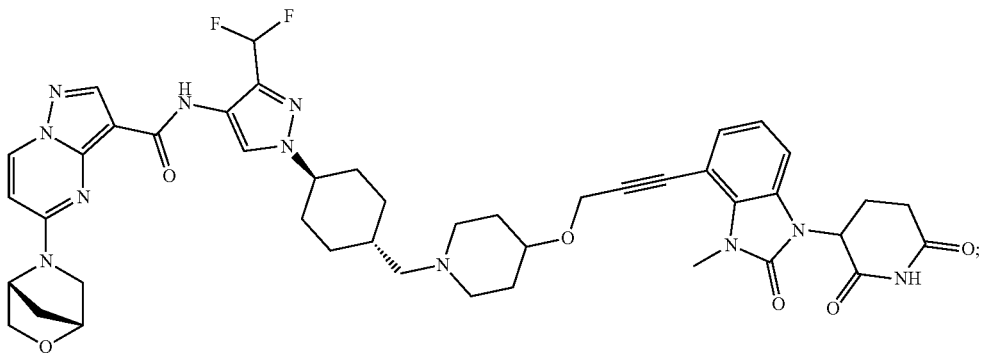 [SMILES: Cn1c(=O)n(C2CCC(=O)NC2=O)c2cccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)c21]

"Compound B" refers to IRAK4 degrader 5-((1R,4R)-2-oxa-5-azabicyclo[2.2.1]heptan-5-yl)-N-(3-(difluoromethyl)-1-((1r,4R)-4-((4-((3-(1-((S)-2,6-dioxopiperidin-3-yl)-3-methyl-2-oxo-2,3-dihydro-1H-benzo[d]imidazol-4-yl)prop-2-yn-1-yl)oxy)piperidin-1-yl)methyl)cyclohexyl)-1H-pyrazol-4-yl)pyrazolo[1,5-a]pyrimidine-3-carboxamide, of formula:

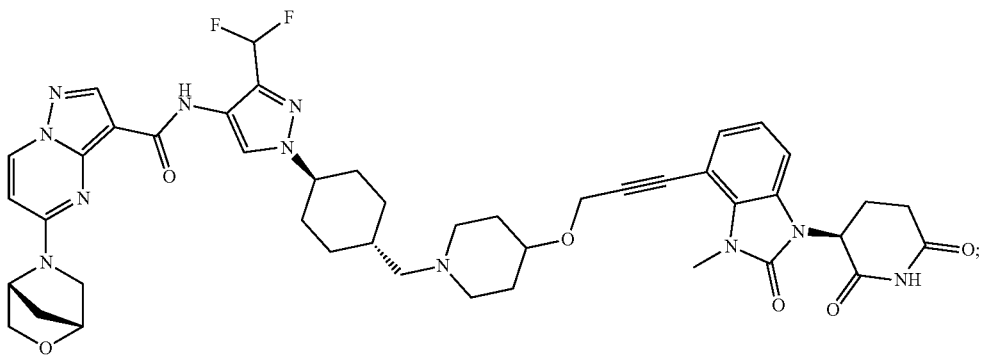 [SMILES: Cn1c(=O)n([C@H]2CCC(=O)NC2=O)c2cccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)c21]

and "Compound C" refers the IRAK4 degrader 5-((1R,4R)-2-oxa-5-azabicyclo[2.2.1]heptan-5-yl)-N-(3-(difluoromethyl)-1-((1r,4R)-4-((4-((3-(1-((R)-2,6-dioxopiperidin-3-yl)-3-methyl-2-oxo-2,3-dihydro-1H-benzo[d]imidazol-4-yl)prop-2-yn-1-yl)oxy)piperidin-1-yl)methyl)cyclohexyl)-1H- pyrazol-4-yl)pyrazolo[1,5-a]pyrimidine-3-carboxamide, of formula:

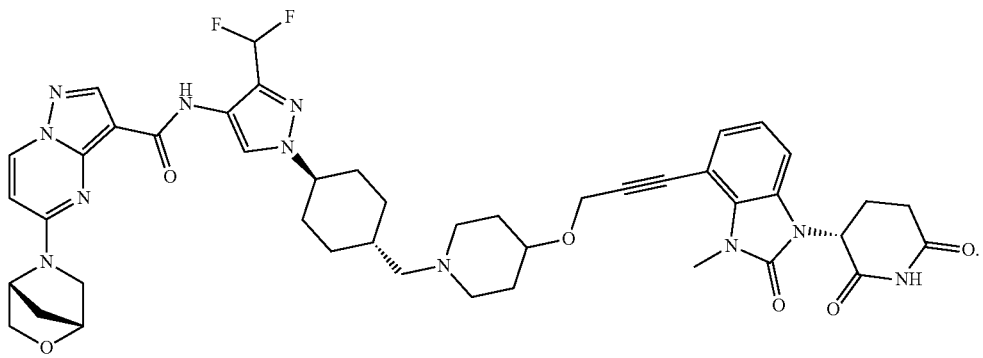 [SMILES: Cn1c(=O)n([C@@H]2CCC(=O)NC2=O)c2cccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)c21]

The molecular structure of Compound A contains three chiral centers, including two fixed/stable centers around the morphine ring (R,R) and one epimerizable chiral center (R/S) resulting in the two diastereomers, (S,R,R)-Compound A and (R,R,R)-Compound A, which are designated as Compound B and Compound C, respectively. In some embodiments, Compound A is Compound B. In some embodiments, Compound A is Compound C. In some embodiments, Compound A is a mixture of Compound B and Compound C. In some embodiments, Compound A is an approximately 1:1 mixture of Compound B and Compound C. Both diastereomers interconvert rapidly in vitro and in vivo. In some embodiments, Compound A, or a pharmaceutically acceptable salt thereof, is amorphous. In some embodiments, Compound A, or a pharmaceutically acceptable salt thereof, is in crystal form. In some embodiments, Compound A is the hydrochloride (HCl) salt. In some embodiments, Compound A HCl salt is amorphous. In some embodiments, Compound A HCl salt is in crystal form.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the terms "about" or "approximately" have the meaning of within 20% of a given value or range. In some embodiments, the term "about" refers to within 20%, 19%, 18%, 17%, 16%, 15%, 14%, 13%, 12%, 11%, 10%, 9%, 8%, 7%, 6%, 5%, 4%, 3%, 2%, or 1% of a given value.

3. Description of Exemplary Methods and Uses

In some embodiments, the present disclosure provides a method of treating an autoimmune/autoinflammatory disease and/or a hematological malignancy, comprising administering to a patient in need thereof a therapeutically effective amount of Compound A, or a pharmaceutically acceptable salt thereof, and/or composition thereof, wherein $C_{max}$ of Compound A in plasma is up to about 561 ng/mL.

In some embodiments, the present disclosure provides a method of treating an autoimmune/autoinflammatory disease and/or a hematological malignancy, comprising administering to a patient in need thereof a therapeutically effective amount of Compound A, or a pharmaceutically acceptable salt thereof, and/or composition thereof, wherein an $AUC_{0-24}$ of Compound A in plasma is up to about 11700 ng*hr/mL.

In some embodiments, an autoimmune/autoinflammatory disease is selected from atopic dermatitis (AD) and hidradenitis suppurativa (HS).

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, a patient or subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment or therapy.

A "therapeutically effective amount" or "therapeutically effective dosage" of a drug or therapeutic agent, such as Compound A, is any amount of the drug that, when used alone or in combination with another therapeutic agent, protects a patient or subject against the onset of a disease, such as AD, or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

In preferred embodiments, a therapeutically effective amount of the drug, such as Compound A, promotes regression to the point of eliminating the disease. In addition, the terms "effective" and "effectiveness" with regard to a treatment includes both pharmacological effectiveness and physiological safety. Pharmacological effectiveness refers to the ability of the Compound A to treat the disease in the patient. Physiological safety refers to the level of toxicity, or other adverse physiological effects at the cellular, organ and/or organism level (adverse effects) resulting from administration of the drug.

As used herein, the terms "therapeutic benefit" or "benefit from therapy" refers to an improvement in one or more of overall survival, progression-free survival, partial response, complete response, and overall response rate and can also include a decrease in severity of disease symptoms, an increase in frequency and duration of disease symptom-free periods, or a prevention of impairment or disability due to the disease affliction.

The term "patient," as used herein, means an animal, preferably a mammal, and most preferably a human.

The term "subject," as used herein, has the same meaning as the term "patient".

4. Pharmacokinetics

In some embodiments, the present disclosure provides a method of administering Compound A to a patient in need thereof, comprising administering to said patient a therapeutically effective amount of Compound A, or a pharmaceutically acceptable salt thereof, and/or composition thereof, wherein a $C_{max}$ of up to about 561 ng/mL of Compound A in plasma is achieved.

In some embodiments, a $C_{max}$ of Compound A in plasma is up to about 550 ng/mL. In some embodiments, a $C_{max}$ of Compound A in plasma is up to about 500 ng/mL. In some embodiments, a $C_{max}$ of Compound A in plasma is up to about 450 ng/mL. In some embodiments, a $C_{max}$ of Compound A in plasma is up to about 400 ng/mL. In some embodiments, a $C_{max}$ of Compound A in plasma is up to about 350 ng/mL. In some embodiments, a $C_{max}$ of Compound A in plasma is up to about 300 ng/mL. In some embodiments, a $C_{max}$ of Compound A in plasma is up to about 250 ng/mL. In some embodiments, a $C_{max}$ of Compound A in plasma is up to about 200 ng/mL. In some embodiments, a $C_{max}$ of Compound A in plasma is up to about 150 ng/mL. In some embodiments, a $C_{max}$ of Compound A in plasma is up to about 100 ng/mL.

In some embodiments, a $C_{max}$ of Compound A in plasma is about 100 ng/mL. In some embodiments, a $C_{max}$ of Compound A in plasma is about 150 ng/mL. In some embodiments, a $C_{max}$ of Compound A in plasma is about 200 ng/mL. In some embodiments, a $C_{max}$ of Compound A in plasma is about 250 ng/mL. In some embodiments, a $C_{max}$ of Compound A in plasma is about 300 ng/mL. In some embodiments, a $C_{max}$ of Compound A in plasma is about 350 ng/mL. In some embodiments, a $C_{max}$ of Compound A in plasma is about 400 ng/mL. In some embodiments, a $C_{max}$ of Compound A in plasma is about 450 ng/mL. In some embodiments, a $C_{max}$ of Compound A in plasma is about 500 ng/mL. In some embodiments, a $C_{max}$ of Compound A in plasma is about 550 ng/mL. In some embodiments, a $C_{max}$ of Compound A in plasma is about 561 ng/mL.

In some embodiments, a $C_{max}$ of Compound A in plasma is about 500 ng/mL to about 561 ng/mL, about 450 ng/mL to about 550 ng/mL, about 400 ng/mL to about 500 ng/mL, about 350 ng/mL to about 450 ng/mL, about 300 ng/mL to about 400 ng/mL, about 250 ng/mL to about 350 ng/mL, about 200 ng/mL to about 300 ng/mL, about 150 ng/mL to about 250 ng/mL, about 100 ng/mL to about 200 ng/mL, or about 50 ng/mL to about 150 ng/mL.

In some embodiments, the present disclosure provides a method of administering Compound A to a patient in need thereof, comprising administering to said patient a therapeutically effective amount of Compound A, or a pharmaceutically acceptable salt thereof, and/or composition thereof, wherein a $C_{max}$ of up to about 288 ng/mL of Compound B in plasma is achieved.

In some embodiments, a $C_{max}$ of Compound B in plasma is up to about 280 ng/mL, up to about 260 ng/mL, up to about 250 ng/mL, up to about 240 ng/mL, up to about 220 ng/mL, up to about 200 ng/mL, up to about 180 ng/mL, up to about 160 ng/mL, up to about 150 ng/mL, up to about 140 ng/mL, up to about 120 ng/mL, or up to about 100 ng/mL.

In some embodiments, a $C_{max}$ of Compound B in plasma is about 280 ng/mL, about 260 ng/mL, about 250 ng/mL, about 240 ng/mL, about 220 ng/mL, about 200 ng/mL, about 180 ng/mL, about 160 ng/mL, about 150 ng/mL, about 140 ng/mL, about 120 ng/mL, or about 100 ng/mL.

In some embodiments, a $C_{max}$ of Compound B in plasma is about 260 ng/mL to about 288 ng/mL, about 240 ng/mL to about 260 ng/mL, about 220 ng/mL to about 240 ng/mL, about 200 ng/mL to about 220 ng/mL, about 180 ng/mL to about 200 ng/mL, about 160 ng/mL to about 180 ng/mL, about 140 ng/mL to about 160 ng/mL, about 120 ng/mL to about 140 ng/mL, about 100 ng/mL to about 120 ng/mL, or about 80 ng/mL to about 100 ng/mL.

In some embodiments, the present disclosure provides a method of administering Compound A to a patient in need thereof, comprising administering to said patient a therapeutically effective amount of Compound A, or a pharmaceutically acceptable salt thereof, and/or composition thereof, wherein a $C_{max}$ of up to about 265 ng/mL of Compound C in plasma is achieved.

In some embodiments, a $C_{max}$ of Compound C in plasma is up to about 260 ng/mL, up to about 250 ng/mL, up to about 240 ng/mL, up to about 220 ng/mL, up to about 200 ng/mL, up to about 180 ng/mL, up to about 160 ng/mL, up to about 150 ng/mL, up to about 140 ng/mL, up to about 120 ng/mL, up to about 100 ng/mL, or up to about 80 ng/mL.

In some embodiments, a $C_{max}$ of Compound C in plasma is about 260 ng/mL, about 250 ng/mL, about 240 ng/mL, about 220 ng/mL, about 200 ng/mL, about 180 ng/mL, about 160 ng/mL, about 150 ng/mL, about 140 ng/mL, about 120 ng/mL, about 100 ng/mL, or about 80 ng/mL.

In some embodiments, a $C_{max}$ of Compound C in plasma is about 240 ng/mL to about 265 ng/mL, about 220 ng/mL to about 240 ng/mL, about 200 ng/mL to about 220 ng/mL, about 180 ng/mL to about 200 ng/mL, about 160 ng/mL to about 180 ng/mL, about 140 ng/mL to about 160 ng/mL, about 120 ng/mL to about 140 ng/mL, about 100 ng/mL to about 120 ng/mL, about 80 ng/mL to about 100 ng/mL, or about 60 ng/mL to about 80 ng/mL.

In some embodiments, the present disclosure provides a method of administering Compound A to a patient in need thereof, comprising administering to said patient a therapeutically effective amount of Compound A, or a pharmaceutically acceptable salt thereof, and/or composition thereof, wherein an $AUC_{0-24}$ of up to about 11700 ng*hr/mL of Compound A in plasma is achieved.

In some embodiments, an $AUC_{0-24}$ of Compound A in plasma is up to about 11500 ng*h/mL, up to about 11000 ng*h/mL, up to about 10500 ng*h/mL, up to about 10000 ng*h/mL, up to about 9500 ng*h/mL, up to about 9000 ng*h/mL, up to about 8500 ng*h/mL, up to about 8000 ng*h/mL, up to about 7500 ng*h/mL, up to about 7000 ng*h/mL, up to about 6500 ng*h/mL, up to about 6000 ng*h/mL, up to about 5500 ng*h/mL, up to about 5000 ng*h/mL, up to about 4500 ng*h/mL, up to about 4000 ng*h/mL, up to about 3500 ng*h/mL, or up to about 3000 ng*h/mL.

In some embodiments, an $AUC_{0-24}$ of Compound A in plasma is about 3,000 ng*h/mL, about 3,500 ng*h/mL, or about 4,000 ng*h/mL. In some embodiments, an $AUC_{0-24}$ of Compound A in plasma is about 5,000 ng*h/mL. In some embodiments, an $AUC_{0-24}$ of Compound A in plasma is about 5,500 ng*h/mL. In some embodiments, an $AUC_{0-24}$ of Compound A in plasma is about 6,000 ng*h/mL. In some embodiments, an $AUC_{0-24}$ of Compound A in plasma is about 6,500 ng*h/mL. In some embodiments, an $AUC_{0-24}$ of Compound A in plasma is about 7,000 ng*h/mL. In some embodiments, an $AUC_{0-24}$ of Compound A in plasma is about 7,500 ng*h/mL. In some embodiments, an $AUC_{0-24}$ of Compound A in plasma is about 8,000 ng*h/mL. In some embodiments, an $AUC_{0-24}$ of Compound A in plasma is about 8,500 ng*h/mL. In some embodiments, an $AUC_{0-24}$ of Compound A in plasma is about 9,000 ng*h/mL. In some embodiments, an $AUC_{0-24}$ of Compound A in plasma is about 9,500 ng*h/mL. In some embodiments, an $AUC_{0-24}$ of Compound A in plasma is about 10,000 ng*h/mL. In some embodiments, an $AUC_{0-24}$ of Compound A in plasma is about 10,500 ng*h/mL. In some embodiments, an $AUC_{0-24}$ of Compound A in plasma is about 11,000 ng*h/mL. In some embodiments, an $AUC_{0-24}$ of Compound A in plasma is about 11,500 ng*h/mL. In some embodiments, an $AUC_{0-24}$ of Compound A in plasma is about 11,700 ng*h/mL.

In some embodiments, an $AUC_{0-24}$ of Compound A in plasma is about 11,000 ng*h/mL to about 11,700 ng*h/mL, about 10,000 ng*h/mL to about 11,000 ng*h/mL, about 9,000 ng*h/mL to about 10,000 ng*h/mL, about 8,000 ng*h/mL to about 9,000 ng*h/mL, about 7,000 ng*h/mL to about 8,000 ng*h/mL, about 6,000 ng*h/mL to about 7,000 ng*h/mL, about 5,000 ng*h/mL to about 6,000 ng*h/mL, or about 4,000 ng*h/mL to about 5,000 ng*h/mL.

In some embodiments, the present disclosure provides a method of administering Compound A to a patient in need thereof, comprising administering to said patient a therapeutically effective amount of Compound A, or a pharmaceutically acceptable salt thereof, and/or composition thereof, wherein an $AUC_{0-24}$ of up to about 6090 ng*h/mL of Compound B in plasma is achieved.

In some embodiments, an $AUC_{0-24}$ of Compound B in plasma is up to about 6000 ng*h/mL, up to about 5500 ng*h/mL, up to about 5000 ng*h/mL, up to about 4500 ng*h/mL, up to about 4000 ng*h/mL, up to about 3500 ng*h/mL, up to about 3000 ng*h/mL, up to about 2500 ng*h/mL, up to about 2000 ng*h/mL, or up to about 1500 ng*h/mL.

In some embodiments, an $AUC_{0-24}$ of Compound B in plasma is about 6000 ng*h/mL, about 5500 ng*h/mL, about 5000 ng*h/mL, about 4500 ng*h/mL, about 4000 ng*h/mL, about 3500 ng*h/mL, about 3000 ng*h/mL, about 2500 ng*h/mL, about 2000 ng*h/mL, or about 1500 ng*h/mL.

In some embodiments, an $AUC_{0-24}$ of Compound B in plasma is about 5500 ng*h/mL to about 6090 ng*h/mL, about 5000 ng*h/mL to about 5500 ng*h/mL, about 4500 ng*h/mL to about 5000 ng*h/mL, about 4000 ng*h/mL to about 4500 ng*h/mL, about 3500 ng*h/mL to about 4000 ng*h/mL, about 3000 ng*h/mL to about 3500 ng*h/mL, about 2500 ng*h/mL to about 3000 ng*h/mL, about 2000 ng*h/mL to about 2500 ng*h/mL, or about 1500 ng*h/mL to about 2000 ng*h/mL.

In some embodiments, the present disclosure provides a method of administering Compound A to a patient in need thereof, comprising administering to said patient a therapeutically effective amount of Compound A, or a pharmaceutically acceptable salt thereof, and/or composition thereof, wherein an $AUC_{0-24}$ of up to about 5620 ng*h/mL of Compound C in plasma is achieved.

In some embodiments, an $AUC_{0-24}$ of Compound C in plasma is up to about 5500 ng*h/mL, up to about 5000 ng*h/mL, up to about 4500 ng*h/mL, up to about 4000 ng*h/mL, up to about 3500 ng*h/mL, up to about 3000 ng*h/mL, up to about 2500 ng*h/mL, up to about 2000 ng*h/mL, or up to about 1500 ng*h/mL.

In some embodiments, an $AUC_{0-24}$ of Compound C in plasma is about 5620 ng*h/mL, about 5500 ng*h/mL, about 5000 ng*h/mL, about 4500 ng*h/mL, about 4000 ng*h/mL, about 3500 ng*h/mL, about 3000 ng*h/mL, about 2500 ng*h/mL, about 2000 ng*h/mL, or about 1500 ng*h/mL.

In some embodiments, an $AUC_{0-24}$ of Compound C in plasma is about 5000 ng*h/mL to about 5620 ng*h/mL, about 4500 ng*h/mL to about 5000 ng*h/mL, about 4000 ng*h/mL to about 4500 ng*h/mL, about 3500 ng*h/mL to about 4000 ng*h/mL, about 3000 ng*h/mL to about 3500 ng*h/mL, about 2500 ng*h/mL to about 3000 ng*h/mL, about 2000 ng*h/mL to about 2500 ng*h/mL, or about 1500 ng*h/mL to about 2000 ng*h/mL.

In some embodiments, the present methods and uses achieve two, three, four, five, or six of the following PK parameters:

a $C_{max}$ of Compound A in plasma
a $C_{max}$ of Compound B in plasma
a $C_{max}$ of Compound C in plasma
an $AUC_{0-24}$ of Compound A in plasma
an $AUC_{0-24}$ of Compound B in plasma
an $AUC_{0-24}$ of Compound C in plasma wherein each of the PK parameters is independently selected from those as described herein.

In certain embodiments of the present methods and uses, Compound A is administered to a patient in thereof at a dose to achieve a $C_{max}$ of Compound A or a therapeutically effective $AUC_{0-24}$ of Compound A. In such embodiments, Compound A is administered at a dose of about 10 mg/kg to about 200 mg/kg, for example, Compound A is administered at a dose selected from about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, and about 90 mg/kg.

In some embodiments, Compound A is administered at a dose of about 20 mg/kg to about 60 mg/kg. In such embodiments, Compound A is administered at a dose of about 25 mg/kg to about 65 mg/kg. In some embodiments, Compound A is administered at a dose of about 30 mg/kg to about 70 mg/kg. In some embodiments, Compound A is administered at a dose of about 35 mg/kg to about 75 mg/kg. In such embodiments, Compound A is administered at a dose of about 40 mg/kg to about 80 mg/kg. In some embodiments, Compound A is administered at a dose of about 45 mg/kg to about 85 mg/kg. In such embodiments, Compound A is administered at a dose of about 50 mg/kg to about 90 mg/kg. In some embodiments, Compound A is administered at a dose of about 55 mg/kg to about 95 mg/kg. In such embodiments, Compound A is administered at a dose of about 60 mg/kg to about 100 mg/kg.

In some embodiments, Compound A is administered at a dose of about 30 mg/kg. In some embodiments, Compound A is administered at a dose of about 35 mg/kg. In some embodiments, Compound A is administered at a dose of about 40 mg/kg. In some embodiments, Compound A is administered at a dose of about 45 mg/kg. In some embodiments, Compound A is administered at a dose of about 50 mg/kg. In some embodiments, Compound A is administered at a dose of about 55 mg/kg. In some embodiments, Compound A is administered at a dose of about 60 mg/kg. In some embodiments, Compound A is administered at a dose of about 65 mg/kg. In some embodiments, Compound A is administered at a dose of about 70 mg/kg. In some embodiments, Compound A is administered at a dose of about 75 mg/kg. In some embodiments, Compound A is administered at a dose of about 80 mg/kg. In some embodiments, Compound A is administered at a dose of about 85 mg/kg. In some embodiments, Compound A is administered at a dose of about 90 mg/kg. In some embodiments, Compound A is administered at a dose of about 95 mg/kg. In some embodiments, Compound A is administered at a dose of about 100 mg/kg. In certain embodiments, Compound A is administered at a dose of about 60 mg/kg per dose.

In certain embodiments of the present methods and uses, the $T_{max}$ of Compound A is achieved in about 4 hrs to about 12 hrs, for example, about 4, about 5, about 6, about 7, about 8, about 9, about 10, about 11, or about 12 hrs. In some embodiments, the $T_{max}$ of Compound A is achieved in about 4 hrs. In some embodiments, the $T_{max}$ of Compound A is achieved in about 5 hrs. In some embodiments, the $T_{max}$ of Compound A is achieved in about 6 hrs. In some embodiments, the $T_{max}$ of Compound A is achieved in about 74 hrs. In some embodiments, the $T_{max}$ of Compound A is achieved in about 8 hrs. In some embodiments, the $T_{max}$ of Compound A is achieved in about 9 hrs. In some embodiments, the $T_{max}$ of Compound A is achieved in about 10 hrs. In some embodiments, the $T_{max}$ of Compound A is achieved in about 11 hrs. In some embodiments, the $T_{max}$ of Compound A is achieved in about 12 hrs.

In certain embodiments of the present methods and uses, the t½ of Compound A is about 5 hrs to 10 hrs. In some embodiments, t½ is about 5 hrs. In some embodiments, t½ is about 6 hrs. In some embodiments, t½ is about 7 hrs. In some embodiments, t½ is about 8 hrs. In some embodiments, t½ is about 9 hrs In some embodiments, t½ is about 10 hrs.

5. Dosing

In some embodiments of the present methods and uses, Compound A, or a pharmaceutically acceptable salt thereof, and/or composition thereof is administered (e.g., orally) to the patient in need thereof.

In some embodiments, a method of the present disclosure comprises orally administering to a patient up to about 10,000 mg of Compound A, or a pharmaceutically acceptable salt thereof, for example up to about 500 mg, up to about 1,000 mg, up to about 1,500 mg, up to about 2,000 mg, up to about 2,500 mg, up to about 3,000 mg, up to about 3,500 mg, up to about 4,000 mg, up to about 4,500 mg, up to about 5,000 mg, up to about 5,500 mg, up to about 6,000 mg, up to about 6,500 mg, up to about 7,000 mg, up to about 7,500 mg, up to about 8,000 mg, up to about 8,500 mg, up to about 9,000 mg, up to about 9,500 mg, or up to about 10,000 mg of Compound A, or a pharmaceutically acceptable salt thereof, and/or composition thereof. In some embodiments, a method of the present disclosure comprises administering to a patient about 500-5,000 mg (for example, about 1,000 to about 4,000 mg, about 1,000 to about 4,000 mg, about 1,000 to about 4,000 mg, about 1,000 to about 4,000 mg, about 1,000 to about 4,000 mg, about 1,000 to about 4,000 mg, or about 1,000 to about 4,000 mg) of Compound A, or a pharmaceutically acceptable salt thereof, and/or composition thereof. For example, in some embodiments, a method of the present disclosure comprises administering to a patient about 3,000 mg of Compound A, or a pharmaceutically acceptable salt thereof, and/or composition thereof, for example in a single 3,000 mg dose. In some embodiments, a method of the present disclosure comprises administering daily to a patient about 3,000 mg of Compound A, or a pharmaceutically acceptable salt thereof, and/or composition thereof, for example as two 1,500 mg doses. In some embodiments, a method of the present disclosure comprises administering daily to a patient about 3,000 mg of Compound A, or a pharmaceutically acceptable salt thereof, and/or composition thereof, for example as three 1,000 mg doses. In some embodiments, a method of the present disclosure comprises administering Compound A, or a pharmaceutically acceptable salt thereof, and/or composition thereof as described herein once daily. In some embodiments, a method of the present disclosure comprises administering a Compound A, or a pharmaceutically acceptable salt thereof, and/or composition thereof as described herein twice daily. In some embodiments, a method of the present disclosure comprises administering a Compound A, or a pharmaceutically acceptable salt thereof, and/or composition thereof as described herein three times daily. In some embodiments, a method of the present disclosure comprises administering a Compound A, or a pharmaceutically acceptable salt thereof, and/or composition thereof as described herein four to fourteen times daily.

In some embodiments, where the patient is administered daily about 600 mg of Compound A, or a pharmaceutically acceptable salt thereof, the dosing is twice daily or BID, i.e., two separate about 300 mg doses. In some embodiments, where the patient is administered daily about 600 mg of Compound A, or a pharmaceutically acceptable salt thereof, the dosing is thrice daily or TID, i.e., three separate about 200 mg doses. In some embodiments, where the patient is administered daily about 600 mg of Compound A, or a pharmaceutically acceptable salt thereof, the dosing is four-times daily or QID, i.e., four separate about 150 mg doses.

In some embodiments, where the patient is administered daily about 800 mg of Compound A, or a pharmaceutically acceptable salt thereof, the dosing is twice daily or BID, i.e., two separate about 400 mg doses. In some embodiments, where the patient is administered daily about 800 mg of Compound A, or a pharmaceutically acceptable salt thereof, the dosing is thrice daily or TID, i.e., three separate about 267 mg doses. In some embodiments, where the patient is administered daily about 800 mg of Compound A, or a pharmaceutically acceptable salt thereof, the dosing is four-times daily or QID, i.e., four separate about 200 mg doses.

In some embodiments, where the patient is administered daily about 1000 mg of Compound A, or a pharmaceutically acceptable salt thereof, the dosing is twice daily or BID, i.e., two separate about 500 mg doses. In some embodiments, where the patient is administered daily about 1000 mg of Compound A, or a pharmaceutically acceptable salt thereof, the dosing is thrice daily or TID, i.e., three separate about 333 mg doses. In some embodiments, where the patient is administered daily about 1000 mg of Compound A, or a pharmaceutically acceptable salt thereof, the dosing is four-times daily or QID, i.e., four separate about 250 mg doses.

In some embodiments, where the patient is administered daily about 1200 mg of Compound A, or a pharmaceutically acceptable salt thereof, the dosing is twice daily or BID, i.e., two separate about 600 mg doses. In some embodiments, where the patient is administered daily about 1200 mg of Compound A, or a pharmaceutically acceptable salt thereof, the dosing is thrice daily or TID, i.e., three separate about 400 mg doses. In some embodiments, where the patient is administered daily about 1200 mg of Compound A, or a pharmaceutically acceptable salt thereof, the dosing is four-times daily or QID, i.e., four separate about 300 mg doses.

In some embodiments, where the patient is administered daily about 1400 mg of Compound A, or a pharmaceutically acceptable salt thereof, the dosing is twice daily or BID, i.e., two separate about 700 mg doses. In some embodiments, where the patient is administered daily about 1400 mg of Compound A, or a pharmaceutically acceptable salt thereof, the dosing is thrice daily or TID, i.e., three separate about 467 mg doses. In some embodiments, where the patient is administered daily about 1400 mg of Compound A, or a pharmaceutically acceptable salt thereof, the dosing is four-times daily or QID, i.e., four separate about 350 mg doses.

In some embodiments, where the patient is administered daily about 1600 mg of Compound A, or a pharmaceutically acceptable salt thereof, the dosing is twice daily or BID, i.e., two separate about 800 mg doses. In some embodiments, where the patient is administered daily about 1600 mg of Compound A, or a pharmaceutically acceptable salt thereof, the dosing is thrice daily or TID, i.e., three separate about 533 mg doses. In some embodiments, where the patient is administered daily about 1600 mg of Compound A, or a pharmaceutically acceptable salt thereof, the dosing is four-times daily or QID, i.e., four separate about 400 mg doses.

In some embodiments, a method of the present disclosure comprises orally administering about 100 mg, about 150 mg, about 200 mg, about 300 mg, about 400 mg, about 500 mg, about 600 mg, about 800 mg, about 1000 mg, about 1200 mg, or about 1400 of Compound A, or a pharmaceutically acceptable salt thereof, and/or composition thereof, once a day in a single dose.

In some embodiments, a method of the present disclosure comprises administering a Compound A, or a pharmaceutically acceptable salt thereof, and/or composition thereof as described herein, wherein there is about 4-24 hours between two consecutive administrations. In some embodiments, there is about 4 hrs, about 6 hrs, about 8 hrs, about 12 hrs, about 18 hrs, or about 24 hrs between two consecutive administrations.

In some embodiments, a method of the present disclosure comprises administering a Compound A, or a pharmaceutically acceptable salt thereof, and/or composition thereof as described herein, wherein there are about 1-7 days between two consecutive administrations. In some embodiments, there are about 1, about 2, about 3, about 4, about 5, about 6, or about 7 days between two consecutive administrations.

In some embodiments, a method of the present disclosure comprises administering a Compound A, or a pharmaceutically acceptable salt thereof, and/or composition thereof as described herein, wherein there is about 1-4 weeks between two consecutive administrations. In some embodiments, there is about 1, about 2, about 3, or about 4 weeks between two consecutive administrations.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated.

6. Pharmaceutically Acceptable Compositions

According to another embodiment, the methods of the present disclosure are practiced by administering a composition comprising Compound A, or a pharmaceutically acceptable salt thereof, and a pharmaceutically acceptable carrier, adjuvant, or vehicle.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this disclosure include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In certain embodiments, pharmaceutically acceptable compositions of this disclosure are formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

Pharmaceutically acceptable compositions of this disclosure can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, Compound A may be administered orally at a dose of about 10 mg/kg to about 200 mg/kg, particularly at a dose of selected from about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, and about 90 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of Compound A, it may be desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this disclosure with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Compound A, or a pharmaceutically acceptable salt thereof, can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this disclosure. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

7. Methods and Uses for Treating Disease

In some embodiments, the present disclosure provides a method of administering Compound A to a patient in need thereof, wherein the patient suffers from an autoimmune/autoinflammatory disease or a hematological malignancy. In some embodiments, the autoimmune/autoinflammatory disease is a cutaneous autoimmune/autoinflammatory disease.

In some embodiments, the autoimmune/autoinflammatory disease includes inflammatory or allergic conditions of the skin, for example psoriasis, generalized pustular psoriasis (GPP), psoriasis *vulgaris*, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, *Pemphigus vulgaris, Pemphigus foliaceus*, paraneoplastic *pemphigus*, epidermolysis bullosa acquisita, acne *vulgaris*, hidradenitis suppurativa, Sweet Syndrome, pyoderma gangrenosum, and other inflammatory or allergic conditions of the skin. In some embodiments, the inflammatory disease of the skin is selected from contact dermatitits, atopic dermatitis, alopecia areata, erythema multiforma, dermatitis herpetiformis, scleroderma, vitiligo, hypersensitivity angiitis, urticaria, bullous pemphigoid, *Pemphigus vulgaris, Pemphigus foliaceus*, paraneoplastic *pemphigus*, epidermolysis bullosa acquisita, or hidradenitis suppurativa.

In some embodiments, the Compound A may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this disclosure is selected from acute and chronic gout, chronic gouty arthritis, psoriasis, psoriatic arthritis, rheumatoid arthritis, juvenile rheumatoid arthritis, systemic juvenile idiopathic arthritis (SJIA), cryopyrin associated periodic syndrome (CAPS), adult onset Still's disease, macrophage activation syndrome (MAS), primary and secondary hemophagocytic lymphohistiocytosis (HLH), familial Mediterranean fever, NLRP12 autoinflammatory syndrome, and osteoarthritis.

In some embodiments the inflammatory disease which can be treated is a TH17 mediated disease. In some embodiments the TH17 mediated disease is selected from systemic lupus erythematosus, multiple sclerosis, psoriasis *vulgaris*, hidradenitis suppurativa, and inflammatory bowel disease (including Crohn's disease or ulcerative colitis).

In some embodiments the inflammatory disease which can be treated according to the methods of this disclosure is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis or chronic rhinosinusitis with nasal polyps (CRSwNP).

In some embodiments, the present disclosure provides a method for treating a cutaneous autoimmune/autoinflammatory disease in a patient, such as atopic dermatitis (AD) and hidradenitis suppurativa (HS), comprising administering to the patient a therapeutically effective amount of Compound A, or a pharmaceutically acceptable salt thereof.

In some embodiments, the present disclosure provides a method for treating AD in a patient, comprising administering to the patient a therapeutically effective amount of Compound A, or a pharmaceutically acceptable salt thereof.

In some embodiments, the present disclosure provides a method for treating HS in a patient, comprising administering to the patient a therapeutically effective amount of Compound A, or a pharmaceutically acceptable salt thereof.

In some embodiments, the present disclosure provides a method for treating rheumatoid arthritis (RA) in a patient, comprising administering to the patient a therapeutically effective amount of Compound A, or a pharmaceutically acceptable salt thereof.

In some embodiments, the present disclosure provides a method for treating hematological malignancy in a patient, comprising administering to the patient a therapeutically effective amount of Compound A, or a pharmaceutically acceptable salt thereof. In some embodiments, the hematological malignancy is leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenström's macroglobulinemia (WM), splenic marginal zone lymphoma, multiple myeloma, plasmacytoma, intravascular large B-cell lymphoma, AML, or MDS.

The following examples are provided for illustrative purposes only and are not to be construed as limiting this invention in any manner.

EXEMPLIFICATION

Compound A can be prepared by methods known to one of ordinary skill in the art, for example, as described in WO 2019/133531 and WO 2020/010227, the contents of which are incorporated herein by reference in their entireties.

General Abbreviations

- Dead animal; no value
\#, N, No. Number
% RSD Relative standard deviation
%-Diff Percent difference
• No value calculated for mean and standard deviation
a.m. Ante meridian
API Active pharmaceutical ingredient
BID, bid Twice a day
BODYTEMP; Btemp Body temperature
C Comment found at the end of each group for each sex
CAM Covariate-adjusted mean
CANFDAS Canned food assessment
CO Clinical observation
CTLS, ctls Controls
CV Coefficient of variation
DIA Diastolic pressure
DESQUAM Desquamation
DSNG Dosing phase
DSNG X.X Dosing Phase Week X. Day X
DT TY Data type
EP European Pharmacopeia
F Female
FECBOL Number of fecal boli
FGSA Forelimb grip strength average (2 trials)
FISSUR Fissuring
FOOT1 Foot splay 1
FOOT2 Foot splay 2
FORE1 Forelimb grip strength 1
FORE2 Forelimb grip strength 2
FSA2 Foot splay average (2 trials)
GROOM Number of Grooms
HGSA2 Hindlimb grip strength average (2 trials)
HIND1 Hindlimb grip strength 1
HIND2 Hindlimb grip strength 2
ID Identification
IM Intramuscular
int Interval
IPD Immediate postdose
LAT Latency
LOQ Limit of quantitation
M Male
MAP Mean arterial pressure
Mean; MEAN Arithmetic mean
N Number of measurements in a group
NA No value; not applicable; not present
ND None detected
NF National Formulary
NVL No visible lesions
Obs Observations
OD Right eye
OS Left eye
OU Both eyes
OXSA Blood oxygen saturation
P Present
P(DR) P value (dose response)
P(overall) Overall P value for all groups
P(v1) P value (versus group 1)
p.m. Post meridian
PD Postdose
PRED Predose phase
PRED X.X Predose Phase Week X. Day X
RBW Rodent Body Weight
REAR Number of rears
RECO Recovery phase
RECO X.X Recovery Phase Week X. Day X
RESP Respiration rate
S.E.M./SEM Standard error mean
SD; S.D.; STAND Standard deviation (when used in numerical data tables) DEV; STANDARD DEV; sd; STD.DE
SE; STDERR Standard error
SYS Systolic pressure
TBW Terminal body weight
TK Toxicokinetic
Typ Type
UNSCHED or Unscheduled or scheduled SCHED
URIPOL Number of urine pools
USP United States Pharmacopeia
WK Week
WT Weight
Units of Measure:
amol Attomole
BPM Beats per minute
° C. Degrees Celsius
cm Centimeter
DL, dl, dL Deciliter
EU Ehrlich unit
FL, fl Femtoliter
fmol Femtomole
G, g Gram
H, h, hr Hours
IU International unit
KG, kg Kilogram
L Liter
MCG, UG, µg, ug Microgram
MEQ Milliequivalent
MG, mg Milligram
MI Million
ML, mL, ml Milliliter
mm Millimeter
mmHG/mmHg Millimeter of mercury
MMOL, mmol Millimole
MN, min Minute
MOS Milliosmole
Msec, msec Millisecond
mU Milliunit
ng Nanogram
PG, pg Picogram
pmol Picomole
PPM, ppm Parts per million
S, s, sec Seconds
TH Thousand
U Units
UL, µL, uL Microliter
UMOL, µmol Micromole
um, µm Micrometer
Veterinary Abbreviations
A Assessment
AU Auris utraque (both ears)
AWCM Animal Welfare and Comparative Medicine
BAR Bright, alert, and responsive
BCS Body condition score
BW Body weight
CRT Capillary refill time
DLAM Department of Laboratory Animal Medicine
FC Food consumption
HC Hydrocortisone
IM Intramuscular
IV Intravenous NHP Nonhuman primate
NSAID Nonsteroidal anti-inflammatory drug
MM Mucous membranes
P Plan
QAR Quiet, alert, and responsive
QFC Qualitative food consumption
RR Respiration rate
SC Subcutaneous
SD Study Director (when used in textual data tables)
S/O Subjective/objective observations
SOAP Subjective/objective observations, assessment, plan
TA Test article
TM Test article/material
TX Treatment
VS Veterinary Services
WNL Within normal limits
Toxicokinetic Parameters
$C_{max}$ Maximum observed concentration
DN $C_{max}$ Dose-normalized maximum concentration, calculated as $C_{max}$ dose
$T_{max}$ Time of maximum observed concentration
$AUC_{0-t}$ Area under the curve from time 0 to the time of the last measurable concentration, calculated using the linear trapezoidal rule
$AUC_{0-24}$ Area under the curve from time 0 to 24 hours, calculated using the linear trapezoidal rule
DN $AUC_{0-24}$ Dose-normalized $AUC_{0-24}$, calculated as $AUC_{0-24}$/dose
$AUC_{0-inf}$ Area under the curve from time 0 to infinity (Day 1 only), calculated as $AUC_{0-inf} = AUC_{0-t} + Ct/\lambda z$, where Ct was the last observed quantifiable concentration and $\lambda z$ was the elimination rate constant
$t_{1/2}$ Elimination half-life, calculated as $\ln(2)/\lambda z$
AR Accumulation ratio, calculated as (Day 8, 28, or 42 $C_{max}$ or $AUC_{0-24}$)/(Day 1 or 15 $C_{max}$ or $AUC_{0-24}$)
I:P Isomer to Parent ratio, calculated as (Isomer $C_{max}$ or $AUC_{0-24}$)/(Parent $C_{max}$ or $AUC_{0-24}$)

Example 1. 4-Week Oral Gavage Toxicity and Toxicokinetic Study with Compound A in Dogs with a 2-Week Recovery The purpose of this study was to evaluate the toxicity and determine the Toxicokinetics (TK) of the test article, Compound A, when administered once daily via oral gavage to dogs for up to 4 weeks and to assess the reversibility of any effects after a 2-week recovery. Animals were initially administered 5, 30, 200, or 100 mg/kg/dose (originally, only TK collections), with the 200 mg/kg/day dose level reduced to 60 mg/kg/day (200/60 mg/kg/dose) from Days 15 through 42.

Male and female dogs were assigned to five groups, and doses were administered as indicated in Table 1. Animals were dosed via oral gavage once daily, for up to 28 days, up to a volume of 5 mL/kg. The control article was 25% (w/w) Hydroxypropyl-β-cyclodextrin (HPBCD; Kleptose Oral Grade HPB) prepared in reverse osmosis water; pH 3.5±0.1. The vehicle was HPBCD (Kleptose Oral Grade HPB) prepared in reverse osmosis water.

TABLE 1

Dose administration.

| Group[a] | No. of Animals[b] | | Dose Level[c] (mg/kg/dose) | Does Concentration[d,e] (mg/mL) |
|---|---|---|---|---|
| | Male | Female | | |
| 1 (Control) | 5 | 5 | 0 | 0 |
| 2 (Low) | 3 | 3 | 5 | 1/2 |
| 3 (Mid) | 5 | 5 | 30 | 6/12 |
| 4 (High) | 5 | 5 | 200/60 | 40/24 |
| 5 (Mid-High) | 3 | 3 | 100 | 20/20 |

[a]Group 1 were administered control article only. Group 5 animals were sacrificed on Day 11 of the dosing phase.
[b]Animals designated for recovery sacrifice (two animals/sex/group in Groups 1, 3, and 4) underwent 2 weeks of recovery following dose administration.
[c]On Days 1 through 8, doses were administered to animals in Group 4 at a level of 200 mg/kg/dose. Starting on Day 15, doses were administered to animals in Group 4 at a level of 60 mg/kg/dose.
[d]Concentrations were corrected for potency using a correction factor of 5.1813.
[e]On Days 1 through 8, doses were administered to animals in all Groups at a volume of 5 mL/kg. Starting on Day 9, doses were administered to all animals in Groups 1, 2, and 3 at a volume of 2.5 mL/kg. Starting on Day 15, doses were administered to all animals in Group 4 at a volume of 2.5 mL/kg. On Day 9, doses continued to be administered to animals in Group 5 at a volume of 5 mL/kg.

Assessment of toxicity was based on mortality, clinical observations, body weights, food consumption, ophthalmic observations, electrocardiographic (ECG) measurements, and clinical and anatomic pathology. Blood samples were collected for toxicokinetic evaluation.

Results

All formulations from Days 1, 28, and 42 were within 10% of the target concentration (ranging from 96.5 to 103.0% of the theoretical concentration, with a relative standard deviation ranging from 0.5 to 1.7%).

Samples for dose analysis from the formulations prepared for dosing on Days 9 and 15 of the dosing phase were not collected, which was a Protocol deviation. It is expected that the formulations prepared on Days 9 and 15 also met specifications, as the results of the formulations prepared for dosing on Days 1, 28, and 42 all met specifications.

All formulations analyzed met the acceptance criteria for study use, and animals were administered the intended dose.

All concentration values of Compound A, Compound B, and Compound C in the vehicle control group were below the lower limit of quantitation (<1.00 ng/mL).

Sex differences in Compound A, Compound B, and Compound C mean $C_{max}$ and $AUC_{0-24}$ values were less than 2-fold; therefore, results and discussion were based on combined sex values.

Toxicokinetics of Compound A

After oral gavage administration, Compound A was absorbed, with median $T_{max}$ values ranging from 5.00 to 9.00 hours on Day 1, from 5.00 to 12.0 hours on Day 8, 6.00 hours on Day 15 (Group 4 only), 4.00 hours on Day 28 (Groups 2 and 3 only), and 6.00 hours on Day 42 (Group 4 only). After reaching $C_{max}$, Compound A concentrations declined, with mean half-life ($t_{1/2}$) values ranging from 6.54 to 7.60 hours on Day 1, 8.08 hours on Day 8, and 8.19 hours on Day 28. Due to the lack of a distinct elimination phase, estimation of elimination phase half-life ($t_{1/2}$) was not attempted for most profiles. Mean concentration values for Compound A were measurable through 24 hours postdose on all collection intervals.

The mean concentration-time profiles for combined sexes show that mean concentrations of Compound A increased with the increase in dose level from 5 to 100 mg/kg/dose on Days 1 and 8 and from 5 to 30 mg/kg/dose on Day 28. No increase in exposure was observed with a further increase in dose level from 100 to 200 mg/kg/dose on Days 1 and 8.

Mean concentrations of Compound A were generally similar after multiple doses when compared to a single dose.

Exposure, as assessed by Compound A mean $C_{max}$ and $AUC_{0-24}$ values, increased with the increase in Compound A dose level from 5 to 100 mg/kg/dose on Days 1 and 8, and from 5 to 30 mg/kg/dose on Day 28. No increase in exposure was observed with a further increase in dose level from 100 to 200 mg/kg/dose on Days 1 and 8. The increases in Compound A mean $C_{max}$ and $AUC_{0-24}$ values were less than dose proportional.

Compound A mean $C_{max}$ and $AUC_{0-24}$ values were generally higher on Days 8 and 28 when compared to Day 1 at the 30 and 100 mg/kg/dose levels, as applicable, indicating potential accumulation of Compound A after multiple doses in dogs. On Day 8, mean accumulation ratio values ranged from 1.16 to 1.86 for $C_{max}$ and from 1.12 to 2.14 for $AUC_{0-24}$. On Day 28, mean accumulation ratio values were 1.38 and 1.28 for $C_{max}$ and $AUC_{0-24}$, respectively, for Group 2 and 1.96 and 2.12 for $C_{max}$ and $AUC_{0-24}$, respectively, for Group 3.

TABLE 2

Summary of Compound A Toxicokinetic Parameters in Dog Plasma

| Day | Dose Group | Cmpd A Dose Level (mg/kg/dose) | $C_{max}$ (ng/mL) | $T_{max}$ (h) | $AUC_{0-24}$ (h * ng/mL) | $t_{1/2}$ |
|---|---|---|---|---|---|---|
| 1 | 2 | 5 | 83.3 | 5 | 1390 | 7.60 |
|   | 3 | 30 | 292 | 6 | 4880 | 6.54[a] |
|   | 4 | 200 | 351 | 6 | 7190 | NR |
|   | 5 | 100 | 363 | 9 | 7080 | NR |
| 8 | 2 | 5 | 107 | 5 | 1720 | 8.08 |
|   | 3 | 30 | 496 | 5 | 10500 | NR |
|   | 4 | 200 | 531 | 12 | 12000 | NR |
|   | 5 | 100 | 640 | 12 | 14300 | NR |
| 15 | 4 | 60 | 489 | 6 | 10200 | NR |
| 28 | 2 | 5 | 123 | 4 | 1990 | 8.19 |
|   | 3 | 30 | 569 | 4 | 10500 | NR |
| 42 | 4 | 60 | 561 | 6 | 11700 | NR |

NR = Not reported due to the lack of a distinct elimination phase.
Note:
Median values are presented for $T_{max}$.
[a]Represents N = 1

Toxicokinetics of Compound B

After oral gavage administration of Compound A, Compound B appeared in plasma, with median $T_{max}$ values ranging from 6.00 to 9.00 hours on Day 1, and 4.00 hours on Days 8, 15 (Group 4 only), 28 (Groups 2 and 3 only), and 42 (Group 4 only). After reaching $C_{max}$, Compound B concentrations declined, with mean $t_{1/2}$ values of 7.60, 8.18, and 8.19 hours on Days 1, 8, and 28, respectively, for Group 2. Due to the lack of a distinct elimination phase, estimation of elimination phase $t_{1/2}$ was not attempted for most profiles. Mean concentration values for Compound B were measurable through 24 hours postdose on all collection intervals.

Mean concentrations of Compound B generally increased with the increase in Compound A dose level from 5 to 100 mg/kg/dose on Days 1 and 8, and from 5 to 30 mg/kg/dose on Day 28. No increase in exposure was observed with a further increase in dose level from 100 to 200 mg/kg/dose on Days 1 and 8. Mean concentrations of Compound B were generally similar after multiple doses of Compound A when compared to a single dose.

Exposure, as assessed by Compound B mean $C_{max}$ and $AUC_{0-24}$ values, increased with the increase in Compound A dose level from 5 to 100 mg/kg/dose on Days 1 and 8, and from 5 to 30 mg/kg/dose on Day 28. No increase in exposure was observed with a further increase in dose level from 100 to 200 mg/kg/dose on Days 1 and 8. The increases in Compound B mean $C_{max}$ and $AUC_{0-24}$ values were less than dose proportional.

Compound B mean $C_{max}$ and $AUC_{0-24}$ values were generally were generally higher on Days 8 and 28 when compared to Day 1 at the 30 and 100 mg/kg/dose levels, as applicable, indicating potential accumulation of Compound B after multiple doses in dogs. On Day 8, mean accumulation ratio values were 1.10 to 1.07 for $C_{max}$ and $AUC_{0-24}$, respectively, for Group 2 and 1.70 and 1.93 for $C_{max}$ and $AUC_{0-24}$, respectively for Group 3. On Day 28, mean accumulation ratio values were 1.40 and 1.32 for $C_{max}$ and $AUC_{0-24}$ for Groups 2 and 3, respectively, and 1.81 and 1.98 for $C_{max}$ and $AUC_{0-24}$, respectively, for Group 3.

On Day 1, the mean Compound B isomer to parent ratios ranged from 0.621 to 0.677 for $C_{max}$ and from 0.605 to 0.712 for $AUC_{0-24}$. On Day 8, the mean isomer to parent ratios ranged from 0.584 to 0.613 for $C_{max}$ and from 0.571 to 0.595 for $AUC_{0-24}$. On Day 15, the mean isomer to parent ratios were 0.551 for $C_{max}$ and 0.542 for $AUC_{0-24}$ for Group 4. On Day 28, the mean isomer to parent ratios were 0.630 and 0.623 for $C_{max}$ and $AUC_{0-24}$, respectively, for Group 2 and 0.578 and 0.629 for $C_{max}$ and $AUC_{0-24}$, respectively, Group 3. On Day 42, the mean isomer to parent ratios were 0.509 for $C_{max}$ and 0.513 for $AUC_{0-24}$ for Group 4.

TABLE 3

Summary of Compound B Toxicokinetic Parameters in Dog Plasma

| Day | Dose Group | Cmpd A Dose Level (mg/kg/dose) | $C_{max}$ (ng/mL) | $T_{max}$ (h) | $AUC_{0-24}$ (h * ng/mL) | $t_{1/2}$ |
|---|---|---|---|---|---|---|
| 1 | 2 | 5 | 51.7 | 6 | 834 | 7.60 |
|   | 3 | 30 | 177 | 6 | 3170 | NR |
|   | 4 | 200 | 228 | 9 | 4720 | NR |
|   | 5 | 100 | 246 | 6 | 5010 | NR |
| 8 | 2 | 5 | 63.4 | 4 | 1010 | 8.18 |
|   | 3 | 30 | 303 | 4 | 6200 | NR |
|   | 4 | 200 | 311 | 4 | 6830 | NR |
|   | 5 | 100 | 372 | 4 | 8170 | NR |
| 15 | 4 | 60 | 269 | 4 | 5490 | NR |
| 28 | 2 | 5 | 77.7 | 4 | 1250 | 8.19 |
|   | 3 | 30 | 326 | 4 | 6500 | NR |
| 42 | 4 | 60 | 288 | 4 | 6090 | NR |

NR = Not reported due to the lack of a distinct elimination phase.
Note:
Median values are presented for $T_{max}$.
[a] Represents N = 1

Toxicokinetics of Compound C

After oral gavage administration of Compound A, Compound C appeared in plasma, with a median $T_{max}$ value of 6.00 hours on Day 1 and 4.00 hours on Days 8, 15 (Group 4 only), 28 (Groups 2 and 3 only), and 42 (Group 4 only). After reaching $C_{max}$, Compound C concentrations declined, with mean $t_{1/2}$ values ranging from 7.65, 9.11, and 8.06 hours on Days 1, 8, and 28, respectively, for Group 2. Due to the lack of a distinct elimination phase, estimation of elimination phase $t_{1/2}$ was not attempted for most profiles. Mean concentration values for Compound C were measurable through 24 hours postdose on all collection intervals.

Mean concentrations of Compound C generally increased with the increase in Compound A dose level from 5 to 100 mg/kg/dose on Days 1 and 8, and from 5 to 30 mg/kg/dose on Day 28. No increase in exposure was observed with a further increase in dose level from 100 to 200 mg/kg/dose on Days 1 and 8. Mean concentrations of Compound C were generally similar after multiple doses of Compound A when compared to a single dose.

Exposure, as assessed by Compound C mean $C_{max}$ and $AUC_{0-24}$ values, increased with the increase in Compound A dose level from 5 to 100 mg/kg/dose on Days 1 and 8, and from 5 to 30 mg/kg/dose on Day 28. No increase in exposure was observed with a further increase in dose level from 100 to 200 mg/kg/dose on Days 1 and 8. The increases in Compound C mean $C_{max}$ and $AUC_{0-24}$ values were less than dose proportional.

Compound C mean $C_{max}$ and $AUC_{0-24}$ values were generally were generally higher on Days 8 and 28 when compared to Day 1 at the 30 and 100 mg/kg/dose levels, as applicable, indicating potential accumulation of Compound C after multiple doses in dogs. On Day 8, mean accumulation ratio values ranged from 1.11 to 1.63 for $C_{max}$ and from 1.11 to 1.79 for $AUC_{0-24}$. On Day 28, mean accumulation ratio values were 1.45 and 1.36 for $C_{max}$ and $AUC_{0-24}$, respectively for Group 2 and 1.73 and 1.86 for $C_{max}$ and $AUC_{0-24}$, respectively, for Group 3.

On Day 1, the mean Compound C isomer to parent ratios ranged from 0.584 to 0.635 for $C_{max}$ and from 0.597 to 0.655 for $AUC_{0-24}$. On Day 8, the mean isomer to parent ratios ranged from 0.508 to 0.584 for $C_{max}$ and from 0.504 to 0.574 for $AUC_{0-24}$.

On Day 15, the mean isomer to parent ratios were 0.521 for $C_{max}$ and 0.509 for $AUC_{0-24}$ for Group 4. On Day 28, the mean isomer to parent ratios were 0.651 and 0.636 for C. and $AUC_{0-24}$, respectively, for Group 2 and 0.527 and 0.571 for $C_{max}$ and $AUC_{0-24}$, respectively, for Group 3. On Day 42, the mean isomer to parent ratios were 0.476 for $C_{max}$ and 0.481 for $AUC_{0-24}$ for Group 4.

TABLE 4

Summary of Compound C Toxicokinetic Parameters in Dog Plasma

| Day | Dose Group | Cmpd A Dose Level (mg/kg/dose) | $C_{max}$ (ng/mL) | $T_{max}$ (h) | $AUC_{0-24}$ (h * ng/mL) | $t_{1/2}$ |
|---|---|---|---|---|---|---|
| 1  | 2 | 5   | 50.9 | 6 | 800  | 7.65[a] |
|    | 3 | 30  | 166  | 6 | 3040 | NR |
|    | 4 | 200 | 222  | 6 | 4510 | NR |
|    | 5 | 100 | 231  | 6 | 4650 | NR |
| 8  | 2 | 5   | 59.8 | 4 | 952  | 9.11 |
|    | 3 | 30  | 273  | 4 | 5480 | NR |
|    | 4 | 200 | 271  | 4 | 5970 | NR |
|    | 5 | 100 | 325  | 4 | 7210 | NR |
| 15 | 4 | 60  | 245  | 4 | 4980 | NR |
| 28 | 2 | 5   | 77.7 | 4 | 1190 | 8.06 |
|    | 3 | 30  | 290  | 4 | 5790 | NR |
| 42 | 4 | 60  | 265  | 4 | 5620 | NR |

NR = Not reported due to the lack of a distinct elimination phase.
Note:
Median values are presented for $T_{max}$.
[a]Represents N = 1

Sex differences in Compound A, Compound B, and Compound C mean $C_{max}$ and $AUC_{0-24}$ values were less than 2-fold. Exposure, as assessed by Compound A, Compound B, and Compound C mean $C_{max}$ and $AUC_{0-24}$ values, increased with the increase in Compound A dose level from 5 to 100 mg/kg/dose on Days 1 and 8, and from 5 to 30 mg/kg/dose on Day 28. No increase in exposure was observed with a further increase in dose level from 100 to 200 mg/kg/dose on Days 1 and 8. The increases in Compound A, Compound B, and Compound C mean $C_{max}$ and $AUC_{0-24}$ were less than dose proportional. Potential accumulation of Compound A, Compound B, and Compound C, up to 2.14-, 1.98-, and 1.86-fold, respectively, was observed after multiple doses in dogs.

During Days 1 to 8 of the dosing phase, abnormal fecal observations and body weight loss were noted across all groups, including controls, and these observations were likely due to the high concentration (25%) of HPBCD in the formulations. The incidence of abnormal fecal observations was reduced following the dose volume reduction from Day 9 of the dosing phase. Therefore, these observations were considered not Compound A related.

One female administered 100 mg/kg/dose was sacrificed in a moribund condition on Day 4 of the dosing phase with clinical observations of decreased activity, liquid feces, vomitus, dehydration, and tremors; the death of this animal was considered test article related. Obvious Compound A-related organ toxicity was not identified in the unscheduled clinical pathology data collected at the unscheduled interval, and changes (compared with predose phase results) were likely secondary to the clinical moribund condition of the animal (potential hypotension/shock). No macroscopic or microscopic findings were noted that determined the cause of the moribund condition. Slightly to moderately increased lymphocyte apoptosis in all lymphoid tissues were consistent with a stress response rather than a direct effect of Compound A. All animals administered 100 mg/kg/dose were sacrificed on Day 11 of the dosing phase.

The test article-related mortality on Day 4 of the dosing phase for one female administered 100 mg/kg/dose and similar clinical observations (emesis, fecal abnormalities, decreased activity, lower food consumption, and tremors) noted in animals administered ≥100 mg/kg/dose exceeded a maximum tolerated dose. This resulted in the sacrifice on Day 11 of the dosing phase of all animals administered 100 mg/kg/dose (which were originally designated for only TK collections) and high-dose animals (200 mg/kg/dose) having a 1-week dose suspension before resuming dosing at 60 mg/kg/dose for four weeks. The clinical observations resolved in the animals administered 200 mg/kg/dose during the dose suspension period.

All other animals survived to their scheduled sacrifice.

No Compound A-related clinical observations or abnormal ophthalmic observations were noted. No Compound A-related alterations in mean body weight, body weight gain, or food consumption were noted at any dose level. No Compound A-related abnormalities were noted during the dosing phase ECG observation.

No Compound A-related effects in scheduled hematology, coagulation, clinical chemistry, or urinalysis test results were identified.

No Compound A-related organ weight differences or macroscopic observations were noted.

At the unscheduled early termination and terminal sacrifice, Compound A-related microscopic findings included minimal or slight infiltrates of vacuolated macrophages in the lamina propria of the jejunum and ileum of animals administered ≥30 mg/kg/dose and in the duodenum of animals administered 200/60 mg/kg/dose and in one female administered 100 mg/kg/dose. Minimally or slightly increased infiltrates of vacuolated macrophages in the gut-associated lymphoid tissues (GALT)/Peyer's patches of animals administered ≥5 mg/kg/dose and in the mesenteric and mandibular lymph nodes and spleen of animals administered ≥30 mg/kg/dose were also considered Compound A related. In the lung, Compound A-related minimal increases of vacuolated alveolar macrophages were observed in animals administered ≥30 mg/kg/dose. The Compound A-related increases of vacuolated macrophages in the small intestine, lymphoid tissues, and lung were considered nonadverse due to the low severity and lack of associated degenerative or inflammatory changes. This cytoplasmic vacuolation was consistent with phospholipidosis as demonstrated by the ultrastructural (transmission electron microscopy) finding of whorled lamellar bodies (interpreted as myelin figures) within secondary lysosomes in the lung, mesenteric lymph node, and ileum of dogs administered 100 mg/kg/dose Compound A in a prior 2-week oral toxicity and toxicokinetics study (Charles River 20.345; Charles River Laboratories, Inc., 2020).

Slight degeneration (bilateral) of seminiferous tubules in the testes with associated increased cell debris in the epididymides was noted in one peripubertal male administered 200/60 mg/kg/dose. The relationship of this testicular finding to administration of Compound A was unclear since degeneration, exfoliation, and depletion of testicular germinal epithelial cells can be observed in the testes of dogs at this stage of sexual maturity (Lanning et al., 2002) and the incidence of testicular degeneration in this study was within the historical control range for this laboratory.

At the recovery sacrifice, minimal vacuolated macrophages in the small intestine (jejunum and/or ileum), GALT/Peyer's patches, and mandibular lymph nodes of animals administered 30 or 200/60 mg/kg/dose and minimally increased vacuolated macrophages in the lung of one male administered 200/60 mg/kg/dose indicating partial reversal. No increases of vacuolated macrophages were noted in the spleen at either dose level, indicating complete reversal. Minimally or moderately increased infiltrates of vacuolated macrophages in the mesenteric lymph node of one male administered 200/60 mg/kg/dose and females administered 30 or 200/60 mg/kg/dose suggested a lack of reversal after 2 weeks.

In conclusion, male and female beagles were administered control article or Compound A via oral gavage at 100 mg/kg/dose for 10 days, 5 and 30 mg/kg/dose Compound A for 4 weeks, and 200 mg/kg/dose for one week followed by one week dose suspension and then resuming dosing at 60 mg/kg/dose for 4 weeks. The dose level of 60 mg/kg/day was determined to be the no observed adverse effect level (NOAEL) based on no clear or adverse test article-related findings in animals that had been previously dosed for 10 days at 200 mg/kg/dose. The dose levels of 100 and 200 mg/kg/dose were considered adverse due to the mortality at 100 mg/kg/dose, while the 200 mg/kg/dose formulation was not tolerated and necessitated a dose suspension and dose reduction. The dose level of 60 mg/kg/dose corresponded to average, sex-combined, maximum observed concentration ($C_{max}$) and area under the concentration-time curve ($AUC_{0-24}$) values of 561 ng/mL and 11,700 ng*hr/mL, respectively, for Compound A; 288 ng/mL and 6090 ng*hr/mL, respectively, for Compound B; and 265 ng/mL and 5620 ng*hr/mL, respectively, for Compound C on Day 42 of the dosing phase.

While we have described a number of embodiments of this invention, it is apparent that our basic examples may be altered to provide other embodiments that utilize the compounds and methods of this invention. Therefore, it will be appreciated that the scope of this invention is to be defined by the application and claims rather than by the specific embodiments that have been represented by way of example.

The invention claimed is:

1. A method of treating an autoimmune/autoinflammatory disease and/or a hematological malignancy, comprising administering to a patient in need thereof a therapeutically effective amount of Compound A, or a pharmaceutically acceptable salt thereof, and/or composition thereof,
wherein a $C_{max}$ of up to about 561 ng/mL of Compound A in plasma is achieved, and
wherein Compound A is 5-((1R,4R)-2-oxa-5-azabicyclo[2.2.1]heptan-5-yl)-N-(3-(difluoromethyl)-1-((1r,4R)-4-((4-((3-(1-(2,6-dioxopiperidin-3-yl)-3-methyl-2-oxo-2,3-dihydro-1H-benzo[d]imidazol-4-yl)prop-2-yn-1-yl)oxy)piperidin-1-yl)methyl)cyclohexyl)-1H-pyrazol-4-yl)pyrazolo[1,5-a]pyrimidine-3-carboxamide.

2. The method of claim 1, wherein the $C_{max}$ of Compound A in plasma is 500 ng/mL to 561 ng/mL.

3. The method of claim 1, wherein the $C_{max}$ of Compound A in plasma is 450 ng/mL to 550 ng/mL.

4. The method of claim 1, wherein a $C_{max}$ of up to 288 ng/mL of Compound B in plasma is achieved,
wherein Compound B is 5-((1R,4R)-2-oxa-5-azabicyclo[2.2.1]heptan-5-yl)-N-(3-(difluoromethyl)-1-((1r,4R)-4-((4-((3-(1-((S)-2,6-dioxopiperidin-3-yl)-3-methyl-2-oxo-2,3-dihydro-1H-benzo[d]imidazol-4-yl)prop-2-yn-1-yl)oxy)piperidin-1-yl)methyl)cyclohexyl)-1H-pyrazol-4-yl)pyrazolo[1,5-a]pyrimidine-3-carboxamide.

5. The method of claim 4, wherein the $C_{max}$ of Compound B in plasma is 260 ng/mL to 288 ng/mL.

6. The method of claim 4, wherein the $C_{max}$ of Compound B in plasma is 240 ng/mL to 260 ng/mL.

7. The method of claim 1, wherein a $C_{max}$ of up to 265 ng/mL of Compound C in plasma is achieved,
wherein Compound C is 5-((1R,4R)-2-oxa-5-azabicyclo[2.2.1]heptan-5-yl)-N-(3-(difluoromethyl)-1-((1r,4R)-4-((4-((3-(1-((R)-2,6-dioxopiperidin-3-yl)-3-methyl-2-oxo-2,3-dihydro-1H-benzo[d]imidazol-4-yl)prop-2-yn-1-yl)oxy)piperidin-1-yl)methyl)cyclohexyl)-1H-pyrazol-4-yl)pyrazolo[1,5-a]pyrimidine-3-carboxamide.

8. The method of claim 7, wherein the $C_{max}$ of Compound C in plasma is 240 ng/mL to 265 ng/mL.

9. The method of claim 7, wherein the $C_{max}$ of Compound C in plasma is 220 ng/mL to 240 ng/mL.

10. The method of claim 1, wherein the Compound A is administered at a dose of 10 mg/kg to 200 mg/kg.

11. The method of claim 10, wherein the Compound A is administered at a dose selected from the group consisting of about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, and about 90 mg/kg.

12. A method of treating an autoimmune/autoinflammatory disease and/or a hematological malignancy, comprising administering to a patient in need thereof a therapeutically effective amount of Compound A, or a pharmaceutically acceptable salt and/or composition thereof,
wherein an $AUC_{0-24}$ of up to 11700 ng*hr/mL of Compound A in plasma is achieved, and
wherein Compound A is 5-((1R,4R)-2-oxa-5-azabicyclo[2.2.1]heptan-5-yl)-N-(3-(difluoromethyl)-1-((1r,4R)-4-((4-((3-(1-(2,6-dioxopiperidin-3-yl)-3-methyl-2-oxo-2,3-dihydro-1H-benzo[d]imidazol-4-yl)prop-2-yn-1-yl)oxy)piperidin-1-yl)methyl)cyclohexyl)-1H-pyrazol-4-yl)pyrazolo[1,5-a]pyrimidine-3-carboxamide.

13. The method of claim 12, wherein the $AUC_{0-24}$ of Compound A in plasma is 11,000 ng*h/mL to 11,700 ng*h/mL.

14. The method of claim 12, wherein the $AUC_{0-24}$ of Compound A in plasma is 10,000 ng*h/mL to 11,000 ng*h/mL.

15. The method of claim 12, wherein an $AUC_{0-24}$ of up to about 6090 ng*h/mL of Compound B in plasma is achieved, and
   wherein Compound B is 5-((1R,4R)-2-oxa-5-azabicyclo[2.2.1]heptan-5-yl)-N-(3-(difluoromethyl)-1-((1r,4R)-4-((3-(1-((S)-2,6-dioxopiperidin-3-yl)-3-methyl-2-oxo-2,3-dihydro-1H-benzo[d]imidazol-4-yl)prop-2-yn-1-yl)oxy)piperidin-1-yl)methyl)cyclohexyl)-1H-pyrazol-4-yl)pyrazolo[1,5-a]pyrimidine-3-carboxamide.

16. The method of claim 15, wherein the $AUC_{0-24}$ of Compound B in plasma is 5500 ng*h/mL to 6090 ng*h/mL.

17. The method of claim 15, wherein the $AUC_{0-24}$ of Compound B in plasma is 5,000 ng*h/mL to 5500 ng*h/mL.

18. The method of claim 12, wherein an $AUC_{0-24}$ of up to 5620 ng*h/mL of Compound C in plasma is achieved, and
   wherein Compound B is 5-((1R,4R)-2-oxa-5-azabicyclo[2.2.1]heptan-5-yl)-N-(3-(difluoromethyl)-1-((1r,4R)-4-((3-(1-((R)-2,6-dioxopiperidin-3-yl)-3-methyl-2-oxo-2,3-dihydro-1H-benzo[d]imidazol-4-yl)prop-2-yn-1-yl)oxy)piperidin-1-yl)methyl)cyclohexyl)-1H-pyrazol-4-yl)pyrazolo[1,5-a]pyrimidine-3-carboxamide.

19. The method of claim 18, wherein the $AUC_{0-24}$ of Compound C in plasma is 5000 ng*h/mL to 5620 ng*h/mL.

20. The method of claim 18, wherein the $AUC_{0-24}$ of Compound C in plasma is 4500 ng*h/mL to 5,000 ng*h/mL.

21. The method of claim 12, wherein Compound A is administered at a dose of 10 mg/kg to 200 mg/kg.

22. The method of claim 12, wherein Compound A is administered at a dose selected from about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, and about 90 mg/kg.

23. The method of claim 1, wherein the $T_{max}$ of Compound A is achieved in 4 hrs to 12 hrs.

24. The method of claim 1, wherein the autoimmune/autoinflammatory disease is selected from a cutaneous, rheumatic, and gastrointestinal autoimmune/autoinflammatory disease.

25. The method of claim 1, wherein the autoimmune/autoinflammatory disease is a cutaneous autoimmune/autoinflammatory disease selected from atopic dermatitis (AD) and hidradenitis suppurativa (HS).

* * * * *